US005501857A

United States Patent [19]
Zimmer

[11] Patent Number: 5,501,857
[45] Date of Patent: Mar. 26, 1996

[54] ORAL NUTRITIONAL AND DIETARY COMPOSITION

[75] Inventor: William A. Zimmer, Hollandale, Wis.

[73] Assignee: Midwestern Bio-Ag Products & Services, Inc., Blue Mounds, Wis.

[21] Appl. No.: 239,701

[22] Filed: May 9, 1994

Related U.S. Application Data

[63] Continuation-in-part of Ser. No. 920,104, Jul. 24, 1992, Pat. No. 5,310,555.

[51] Int. Cl.$^6$ ..................................................... A23K 1/18
[52] U.S. Cl. .......................... 424/438; 424/451; 424/453; 424/454; 424/456; 426/807
[58] Field of Search ................................. 424/438, 451, 424/453, 454, 456

[56] References Cited

U.S. PATENT DOCUMENTS

| | | | |
|---|---|---|---|
| 1,419,618 | 6/1922 | Deming | 424/451 |
| 1,815,902 | 7/1931 | Ellzey | 424/453 |
| 3,072,528 | 1/1963 | Kludas et al. | 424/451 |
| 3,794,732 | 2/1974 | Raun | 424/283 |
| 3,839,557 | 10/1974 | Raun | 424/115 |

(List continued on next page.)

FOREIGN PATENT DOCUMENTS

| | | |
|---|---|---|
| 2524311 | 10/1983 | France . |
| 7610038 | 3/1978 | Netherlands . |

OTHER PUBLICATIONS

Gilliland, S. E., *8th Int'l. Biotech. Syn. Proc.*, vol. 2, pp. 923–933 (1988).
Aimutis, W. R., "Judging Microbials," *Feeds Management*, vol. 42, pp. 26–32 (1991).
Gedek, B., "Probiotics in Animal Feeding–Effects on Performance and Animal Health," *Feed Magazine International*, Feb., 1987.
Jones, B. E., "Hard Gelatin Capsules and the Pharmaceutical Formulator," *Pharmaceutical Technology*, vol. 9, Issue 9, (1985).
Lund, A., "Yeasts and Moulds in Bovine Rumen," *Journal of General Microbiology* (1974), vol. 81, 453–462.
Dawson, K., "Current and Future Role of Yeast Culture in Animal Production: A Review of Research Over the Last Six Years," *Biotechnology in the Feed Industry—Supplement to the Proceedings of Alltech's 8th Annual Symposium*, pp. 1–23—surveys research from 1985–1991, publication date unknown, document shows 1992 award winner.
Brock & Madigan, *Biology of Microorganisms*, 6th Edition 1991, pp. 639–642.
Dawson, K. "Effects of Microbial Supplements Containing Yeast and Lactobacilli on Roughage–Fed Ruminal Microbial Activities," *J. Anim. Sci.* (1990), vol. 68, pp. 3392–3398.
Torpac, "Pharmaceutical Manufactures' Guide to Large Gelatin Capsule Applications," pp. 1–3, (1987), place of publication: Canada.
Brian Jones, "Capsule Technology" (sheet entitled BIPHASIC FILLING), p. $H_{10}$, (1984), Center for Professional Advancement, East Brunswick, N.J.
Official Publication 1993, Association of American Feed Control Officials Incorporated, "Direct–Fed Microorganisms," pp. 148–149.
Official Publication 1993, Association of American Feed Control Officials Incorporated, "Least Common Feed Ingredients," pp. 248–253.

*Primary Examiner*—D. Gabrielle Phelan
*Attorney, Agent, or Firm*—Teresa J. Welch; Stroud, Stroud, Willink, Thompson & Howard

[57] ABSTRACT

An oral nutritional supplement, i.e., a dietary adjunct, for livestock which includes incompatible live microbial cultures, and vitamin and mineral supplements, each separated from the other via multiple encapsulation. The microbial cultures include gastrointestinal bacteria, yeasts or fungi. A method of delivering incompatible compounds in vivo, a method of preparing shelf-stable compositions of incompatible substances, and a system for delivering oral nutritional supplements to livestock are also provided.

32 Claims, 7 Drawing Sheets

U.S. PATENT DOCUMENTS

| | | | |
|---|---|---|---|
| 4,129,578 | 12/1978 | Celmer et al. | 260/345.7 R |
| 4,138,498 | 2/1979 | Das | 426/807 |
| 4,159,322 | 6/1979 | Cloyd | 424/181 |
| 4,405,609 | 9/1983 | Potter | 424/177 |
| 4,695,466 | 9/1987 | Morishita et al. | 424/456 |
| 4,761,426 | 8/1988 | Martin et al. | 514/460 |
| 5,104,662 | 4/1992 | Kalsta et al. | 424/451 |
| 5,244,669 | 9/1993 | Satoh et al. | 424/438 |
| 5,244,681 | 9/1993 | Vinci et al. | 426/72 |

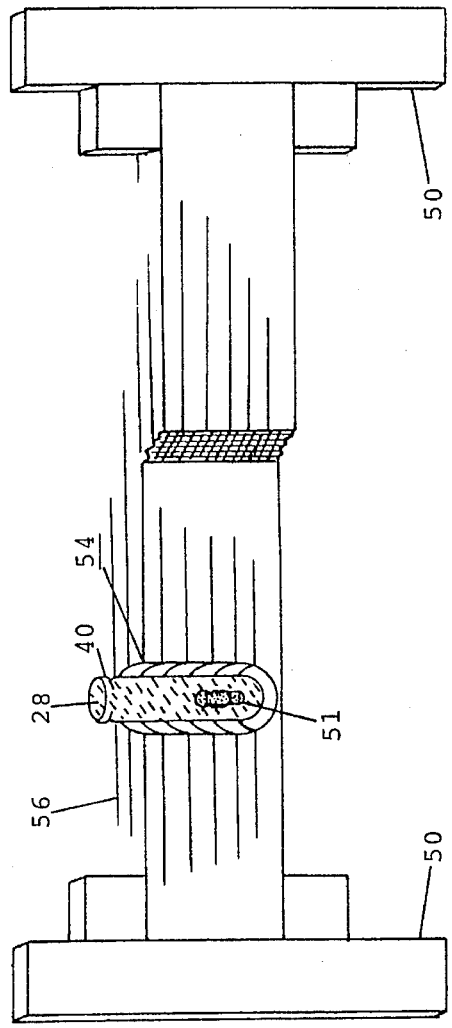
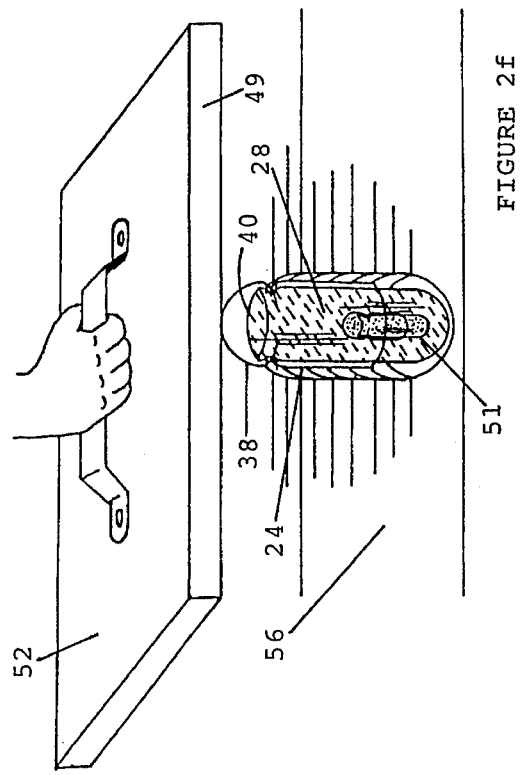
FIGURE 2e
FIGURE 2f

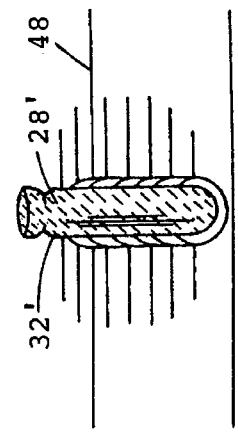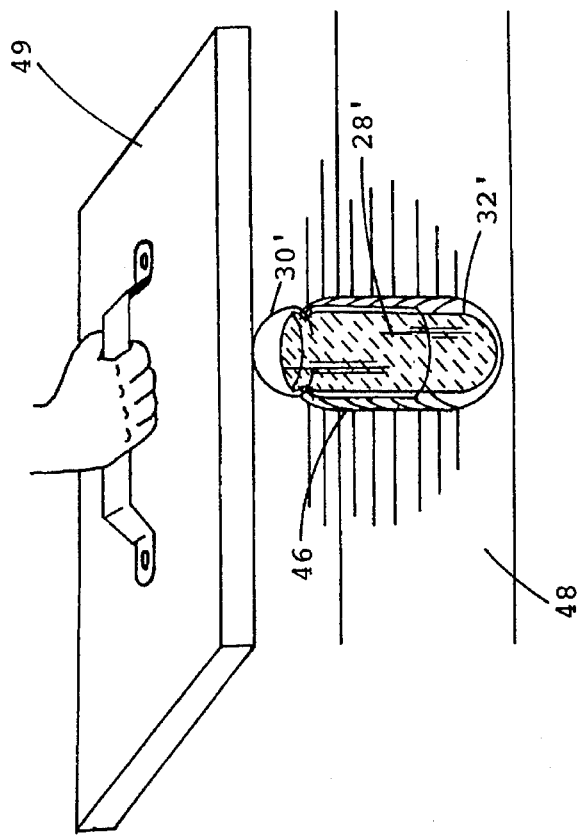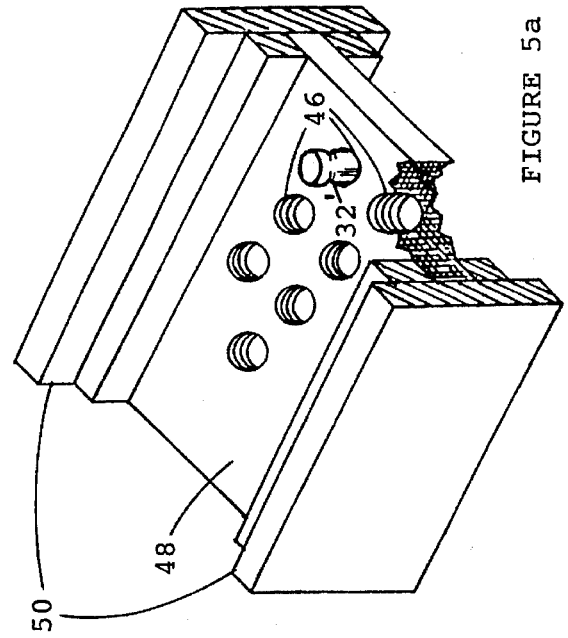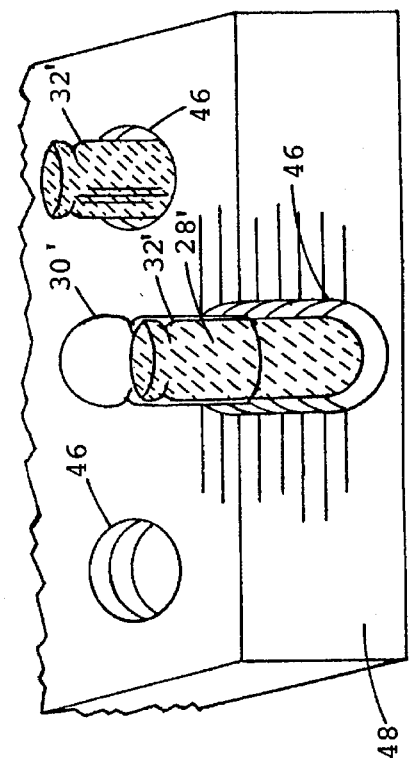

ORAL NUTRITIONAL AND DIETARY COMPOSITION

This application is a continuation-in-part of U.S. patent application Ser. No. 07/920,104 filed Jul. 24, 1992, now U.S. Pat. No. 5,310,555.

TECHNICAL FIELD

This invention relates generally to veterinary nutritional and dietary compositions for livestock, and specifically to compositions which combine incompatible substances such as nutrient supplements and viable direct-fed microbials. The invention also relates to a method of preparing a shelf-stable composition of incompatible agents. The present invention is particularly well suited to deliver in vivo, nearly simultaneously, incompatible supplements such as vitamins and minerals and microorganisms to cattle, sheep, goats, ostriches, and emus in the form of a capsule-in-a-capsule.

BACKGROUND OF THE INVENTION

In the past, the development of effective treatments for feeding disorders in cattle, sheep and goats has been spurred by a desire to maximize yields of meat and dairy products. Existing drug-based treatments (see, e.g., U.S. Pat. No. 4,761,426 issued to Martin, et al., and U.S. Pat. No. 4,405,609 issued to Potter), however, have the serious drawback of rendering products from treated animals unsalable for long periods under laws designed to protect consumers from harmful drug residues. Farmers, unhappy with the need to choose between low yields or unsalable products, have long sought the development of alternative, drug-free dietary treatments. As farmers expand into other livestock markets, such as the raising of ostriches and emus for yields of meat and eggs, similar problems occur. The goals of drug-free dietary treatments are generally, improved growth and performance, and especially, appetite stimulation and reestablishment of the rumen or gastrointestinal microbial populations necessary for proper digestion.

Much attention has been given in recent years to the use of certain microorganisms as dietary adjuncts in efforts to improve the growth and performance of livestock in general, and reestablishment of rumen or gastrointestinal microbial populations in ruminant animals. Such dietary cultures are known as probiotics or direct-fed microbials. (Gilliland, S. E., 8th Int'l. Biotech. Syn. Proc., Vol. 2, pp. 923–933 (1988)). Generally, the microorganisms of such probiotics are those that are expected to grow and/or function in the intestinal tract or in the rumen of the particular animal and can exert certain metabolic actions that influence that animal. Various gastrointestinal tract microorganisms which have been considered for this type of usage include *Lactobacillus acidophilus, Lactobacillus plantarum, Lactobacillus fermentum, Lactobacillus casei, Lactobacillus lactis, Pediococcus cerevisiae* and *Streptococcus faecium*. These bacteria perform one or more of the following functions: They compete for villi attachment sites with pathogenic microorganisms, control Ph(acidity) within the gastrointestinal tract, produce enzymes and other metabolites which benefit digestion, and produce substances capable of inhibiting the growth of other harmful microorganisms. Additional microorganisms that could be used for this purpose include the live cell yeast, *Saccharomyces cerevisiae*, the fungus, *Aspergillus oryzae*, and bacteria, *Bifidobacterium longum* and *Propionibacterium freudenreichii* or the taxonomic equivalents thereof. Live cell yeast cultures and fungi, such as *Saccharomyces cerevisiae* and *Aspergillus oryzae*, have been shown to produce beneficial enzymes and raise the pH in the rumen by enhancing the growth of bacteria that either utilize lactic acid or ferment feedstuffs to absorbable fatty acids. Bifidobacteria species have been shown to be a major colonizer of the undeveloped rumen of newborn cattle and the lower intestine of all newborn animals. *Bifidobacterium longum* may also aid in intestinal/rumen pH control and enzyme production. Certain strains of *Propionibacterium freudenreichii* utilize rumen nitrates as a food substrate and are, therefore, beneficial in reducing nitrate toxicity in animals exposed to excessive amounts of that chemical. This might occur where the cattle are exposed to excess nitrates in feeds, to fresh pastures grown during drought conditions and to nitrates in water.

As known in the art, the Food and Drug Administration, Center for Veterinary Medicine has published a list of microorganisms which they have reviewed and have found to present no safety concerns when used in direct-fed microbial products in the Official Publication of the Association of American Feed Control Officials, Inc. (AAFCO) (1993) at pp. 148–149, the disclosure of which is hereby incorporated by reference. Many commercial direct-fed microbials are especially important in their non-spore forms, i.e. vegetative forms. These vegetative forms may be in the dormant state. These microbials are approved for animal feeding and are available to the public from several suppliers.

Common feed additives (AAFCO p. 248–253, 21 CFR §573 and 21 CFR §584) are known in the art as carriers for animal or livestock feeding purposes. Those which have been found to be safe when used in feed, are on the FDA's Generally Recognized as Safe (GRAS) lists. 21 CFR 584. The ingredient additives not defined by AAFCO appear on the "Least Common Federal Ingredients" list, (AAFCO p. 248–253).

To derive maximum benefit from use of probiotics, the microorganisms must survive and grow in the rumen and/or intestine. It is thus imperative that the probiotic contain viable and active microorganisms at the time of consumption. The microorganisms used as probiotics, therefore, must be stable during preparation and during storage prior to consumption.

The simplest approach to delivery of probiotics is to add cultures to animal feed. However, it appears that few direct-fed microbials are stable in feed for more than 3–5 days. (Aimutis, W. R., *Feeds Management*, Vol. 42, pp. 26–32 (1991)). Moreover, some feed contains antibiotics which are contrary to microbials stability. Yet other feed is pelleted, and most Lactobacillus species, which are predominant and beneficial intestinal species, are susceptible to the high temperatures, compression, aeration and mixing abrasion to which they are exposed during the pelleting process.

Another approach is to provide the bacteria themselves as a pellet or bolus. Many such bolus products are commercially available.

More recently, bolus or pellet formulations have been developed which include a combination of the microorganisms and dry vitamin and trace mineral supplements, as nearly simultaneous administration in vivo of these components has been suggested as being highly beneficial to achieving the goals of appetite stimulation and microbial population reestablishment. Many of these bolus formulations are available commercially. It has been found, however, that the supplements and microorganisms are incompatible as the vitamin and mineral levels commonly used and efficacious for livestock are toxic to the microorganisms in many formulations. The toxicity is dependent upon concentration of the vitamins and/or minerals and the microorganisms used. By "toxic" is meant that the vitamins and/or minerals inhibit, or prevent growth or diminish viability of the microorganisms. By viability is meant the capability of life. The toxicity is demonstrated in a reduction of shelf life of a microorganism. As the time period in which the microbials are in contact with the toxic substance increases, the concentration of the microbials (often expressed as colony forming units per gram i.e., CFU/g or colony forming units per bolus i.e., CFU/Bolus) as measured by standard testing procedures, decreases. This is also expressed as Percent Survival Rate of the microorganism observed over a period of time. As the time period increases, the Percent Survival Rate decreases.

Thus, the CFU's decrease as time increases. The population of viable microorganisms can be greatly reduced within a week or within approximately a month. As indicated previously, microorganisms are also sensitive to mixing abrasion, aeration, compression and high temperatures, all of which occur during conventional hard bolus production. Moreover, the bolus formulations also require binding, wetting and disintegrating agents, any or all of which may adversely affect the viability of the microorganisms. Such bolus products, therefore, have limited shelf stability or shelf life, in that, the population of viable microorganisms can be greatly reduced within about a week or about a month.

Thus, a persistent and vexatious problem, largely unattended by the prior art, is the lack of a method for simultaneously delivering incompatible substances in vivo to animals, when one of the substances is a viable microorganism culture.

Various prior art methods of physical separation, e.g., encoating, encapsulation and microencapsulation, of nutritional supplements are known, however, none adequately address the preparation and storage requirements of sensitive direct-fed microbial agents. For example, conventional microencapsulation subjects microorganisms to a number of potentially fatal packaging procedures and requires expensive materials, complex equipment, and carefully controlled environmental conditions. Polymeric microcapsules also require specific pH ranges or enzyme activities to effect release of their contents in vivo. These requirements often frustrate conventional laboratory assessment techniques and prevent effective nutrient release in animals whose rumen and/or gastrointestinal pH or enzyme balances have been disrupted by microbial depopulation.

U.S. Pat. No. 4,695,466 to Morishita discloses a multiple-encapsulation method. The Morishita process includes successively encapsulating oil solutions or suspensions in soft capsules. Although the method of Morishita has potential for delivery of two components in a single vehicle, the use of oil carriers presents insurmountable obstacles to the delivery of microorganisms and vitamin supplement components. It is unlikely that Morishita's soft outer capsules will be able to withstand common shipping, storage and administration conditions and also is unlikely applicable to commonly available microbial forms.

Despite recognition of the known drawbacks of prior art products, the art has not adequately responded to date with a method for delivery in vivo of the incompatible components, namely, direct-fed microbials and nutrient supplements nearly simultaneously to cattle, sheep, goats, and ratites.

SUMMARY OF THE INVENTION

The present invention responds specifically to the long-felt need heretofore unmet by the prior art, and especially with a view to overcoming the inherent inadequacies of combination supplements and direct-fed microbials for oral delivery to animals. The composition is a dietary adjunct or feedstuff, providing the convenience and reliability of oral administration, while providing near simultaneous delivery in vivo of direct-fed microbials and incompatible substances, such as vitamins and minerals in a partitioned unitary structure, a double capsule. The composition is shelf stable, i.e., allows substantially greater viability of microbials, and does not require binding, wetting and disintegrating agents necessary for pellet or bolus formulations. The composition provides accurate unit dosage, virtually simultaneous in vivo delivery of the components of the double capsule, and rapid in vivo dissolution.

This invention is directed to the probiotic classes of publicly available direct-fed microbials which are fed to both ruminant animals and to non-ruminant animals. Where the direct-fed-microbial is ruminant specific, it is understood that the application is to feeding ruminant animals. However the scope of this invention also includes non-ruminant animals such as other livestock. Other livestock includes, but is not limited to, ratites, such as ostriches and emus.

The foregoing, and other advantages of the present invention, are realized in one aspect thereof in an oral nutritional composition, i.e., a dietary adjunct, useful for treating feeding disorders and improving feed efficiency in livestock, e.g., cattle, sheep and goats, especially ruminants, but not limited to ruminants. Non-ruminants include, but are not limited to ratites (such as, but not limited to ostriches and emus). For ruminant animals, the gastrointestinal tract includes the rumen; for non-ruminant animals, the gastrointestinal tract is absent a rumen. Gastrointestinal microorganisms inhabit the gastrointestinal tract. Gastrointestinal microorganisms include bacteria, live cell yeasts or fungi, among others.

The dietary adjunct composition comprises a double capsule which includes live cultures of rumen and/or gastrointestinal microorganisms in a first capsule which is enclosed with vitamin and/or mineral supplements in a second capsule. The capsules are preferably made of a dissolvable material, preferably gelatin. The microorganisms and supplements may be combined with acceptable feed grade carriers. Gastrointestinal microorganisms, include bacteria, live cell yeasts, fungi or a combination thereof. By live cell yeast is meant, a yeast culture containing live yeast cells but not containing yeast metabolites and/or the yeast growth media.

In another embodiment of this invention, this invention provides a dietary adjunct composition comprising a double capsule which includes a vitamin and/or mineral supplement in a first capsule which is enclosed with live gastrointestinal microorganisms in a second capsule. The first capsule wall separates the live microorganisms from the vitamins and/or minerals. The capsules are preferably made of gelatin. The microorganisms and supplements may be combined with acceptable feed grade carriers. Gastrointestinal microorganisms, include bacteria, live cell yeasts, fungi or a combination thereof. By live cell yeast is meant, a yeast culture containing live yeast cells but not containing yeast metabolites and/or the yeast growth media.

In still another aspect, this invention comprises a double capsule which includes a gastrointestinal microorganism separated by a capsule wall from a feed ingredient which when stored in contact with the microorganism for a period of time will cause the microorganism to diminish its full growth potential.

In still another embodiment, this invention provides a dietary adjunct composition comprising a double capsule which includes an inner capsule and an outer capsule. The outer capsule is spaced apart from and encloses the inner capsule. The inner capsule includes a dissolvable shell and a first substance therein. The outer capsule includes a dissolvable shell and a second substance therein. The shells are preferably made of gelatin. One of the substances is viable gastrointestinal microorganisms and the other substance is a nutritional supplement. The nutritional supplement has the property of diminishing the shelf life of the microorganisms. That is, direct contact between the microorganisms and the nutritional supplement for an extended period of time will cause the number of colony forming units expressed per unit quantity, i.e., CFU/g or CFU/bolus, of the gastrointestinal microorganisms to decrease.

In another aspect, the invention is a method of simultaneously delivering incompatible compounds to animals in vivo. Such delivery is achieved by feeding an animal a double capsule containing a first substance in a first capsule, which is enclosed with a second substance, in a second larger capsule. One of the two substances is a viable substance. The other substance is such that the viable substance is rendered nonviable when both substances are stored and administered simultaneously in a bolus or in a single capsule formulation. By "incompatible" is meant that one of the two substances prevents or inhibits the growth and/or effects the viability of the other substance. By viable is meant capability of life. The substance can come out of a dormant condition, such as a freeze dried state to a active vegetative state. The viable substance is not completely in a spore state. The viable substance may be in a form that has both spore forming and non spore forming components. As is known in the art, only certain of the direct-fed microbials have a spore component. In this instance, CFU include typically spore and nonspore forms.

In another embodiment, this invention provides a method for preparing shelf-stable compositions of incompatible substances, which includes the use of multiple capsules of variable composition. Such method is accomplished manually or by machine.

Other advantages and a fuller appreciation of the specific adaptations, compositional variations, and physical and chemical attributes of the present invention will be gained upon an examination of the following detailed description of the invention, taken in conjunction with the accompanying drawings and appended claims.

BRIEF DESCRIPTION OF THE DRAWINGS

The present invention will hereinafter be described in conjunction with the appended drawings, wherein like designations refer to like elements throughout and in which:

FIGS. 2a–2f illustrate a method by which each capsule-in-a-capsule structure of FIG. 1 is assembled;

FIGS. 5a–5f illustrates a method by which each capsule-in-a-capsule structure of FIG. 4 is assembled.

DETAILED DESCRIPTION

Figure 1:
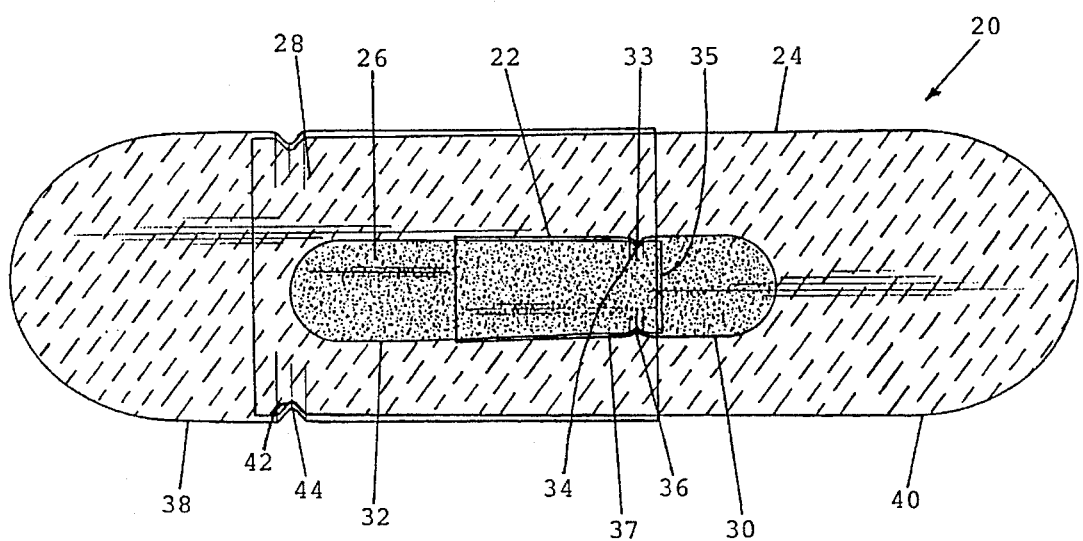
FIG. 1 shows an enlarged sectional view of the capsule-in-a-capsule structure in accordance with the present invention with the microorganisms within the inner capsule.
Figure 2B:
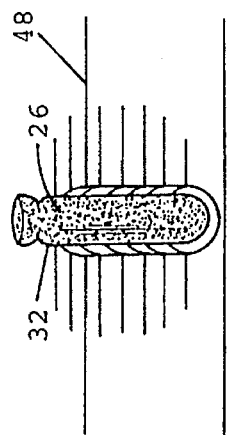
Figure 2D:
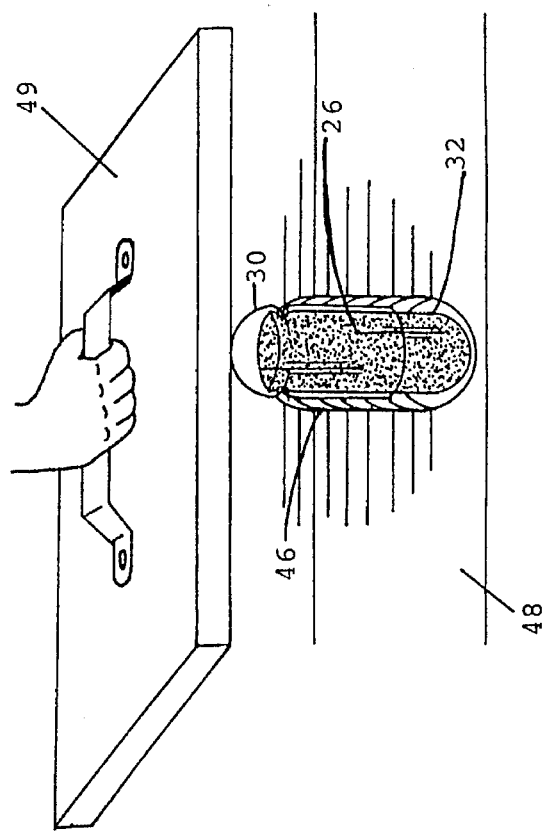
Figure 2A:
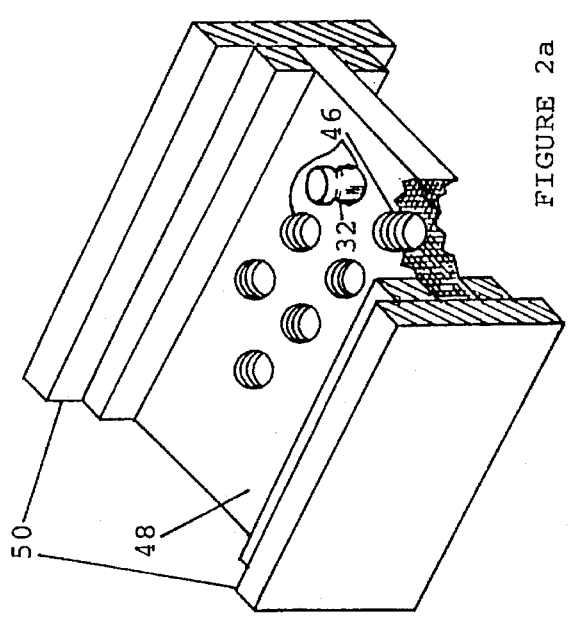
Figure 2C:
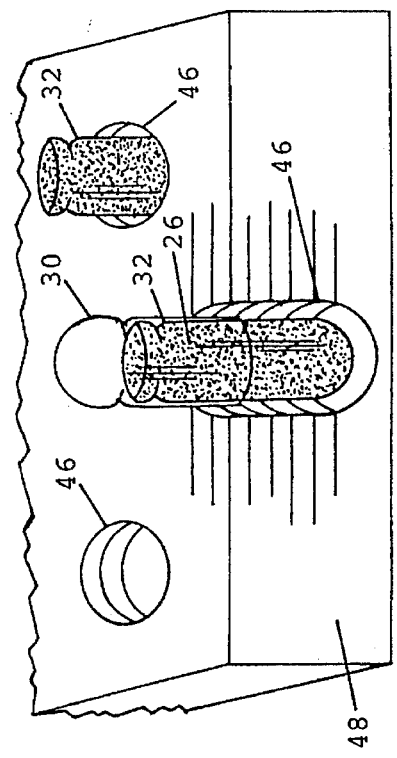

The present invention relates broadly to nutritional supplements and dietary adjuncts for animals, such as cattle, sheep, goats, and ratites and specifically to compositions and nutrient delivery systems which permit delivery of direct-fed microbials with incompatible substances. However, the composition of the present invention is most particularly adapted for use in oral supplementation formulations which combine nutrients, such as vitamins and/or minerals, and viable gastrointestinal microorganisms, such as fungi, yeasts, or bacteria. Gastrointestinal microorganisms include intestinal microorganisms, and/or rumen microorganisms depending upon the animal. The gastrointestinal microorganisms include but are not limited to those dwelling in the stomach, large and small intestines. Accordingly, the present invention will now be described in detail with respect to such fields of endeavor; however, those skilled in the art will appreciate that such description of the invention is meant to be exemplary only and should not be viewed as limitative of the full scope thereof.

The present invention provides a nutritional composition useful for ameliorating drug-induced, stress-related, and other feeding disorders in food-producing animals. The composition is particularly useful as a ruminant feedstuff for improving feed efficiency and promoting growth for cattle, sheep and goats, but may also be used in non-ruminant food producing animals such as ratites. Ratitae is a classification of birds and includes birds, such as ostriches, rheas, cassowaries, emus, eliphantbirds, moas, kiwis. Raising emus and ostriches is popular for production of meat, hides, feathers and eggs. For ruminants, the composition avoids the milk and slaughter withdrawal periods required after drug treatments and enhances the general nutritional status of the animal. Additionally, the composition is shelf-stable and provides a general packaging system for incompatible materials, and is particularly useful for direct-fed microbial agents or probiotics. These attributes are achieved through a particular composition meeting a special combination of physical parameters.

As used herein, the term "incompatible" is meant to refer to substances which deleteriously react with one another when combined in desired levels or concentrations. The microbial is a substance which has a capacity of viability or is viable. The incompatible substance renders the microbial non viable when the probiotic and the incompatible substance are stored and administered simultaneously in a bolus or in a single capsule formulation.

In one embodiment, the invention provides a nutritional composition whose components are incompatible, and which incompatible components are physically separated from each other until they reach their in vivo situs. The composition includes two components. One of the components is cultures of viable microorganisms, e.g., bacteria or fungi or live cell yeasts, or combinations thereof. By live cell yeasts is meant, a yeast culture containing live yeast cells but not containing yeast metabolites and/or the yeast growth media. The other of the components is nutritional supplements, e.g., vitamins and/or minerals. Each component necessary to make and use the present invention is commercially available or can be synthesized using known methodologies. The two components are separated from one another. One of the components is enclosed in the inner capsule. The outer capsule contains the inner capsule and the other component. In a preferred embodiment, the microbial cultures are enclosed in a first capsule which is then enclosed with the vitamin and/or mineral supplements in a second such capsule, i.e., a "capsule-in-a-capsule" structure. However the invention also comprehends the reversal of the components, i.e., the vitamins and/or mineral supplements are enclosed in a first capsule which is then enclosed with the microorganisms in a second capsule. The microorganisms of the one component serve the valuable function of repopulating the rumen and/or intestines, thus enabling digestion to resume, producing digestive enzymes, and correcting acid imbalances which result from rumen or intestinal microbial microorganism depopulation.

The vitamins and/or minerals of the other component increase the nutritional status of animals laboring under conditions of malnutrition caused by feeding disorders. Further, once dispersed throughout the rumen and/or intestines, these vitamins and/or minerals support the rapid growth of the microorganisms of the first component. Oral administration of these vitamins and/or minerals contemporaneously with the administration of microorganisms is preferable to separate administration. Separate administration increases the risk that microorganisms will not encounter dispersed vitamins and minerals in the rumen and/or in the intestine and thus fail to exhibit their full growth potential. Also separate administration increases the end user cost for materials and labor.

In one embodiment, it has been found that the bacterial survival rate with the capsule-in-a-capsule structure of the present invention after up to six months storage, i.e., a shelf-life of six months after preparation, is nearly 500 times that of an admixture of the bacteria and nutrient supplements. An admixture of bacterial and nutrient supplements is typically a single capsule or a bolus formulation.

Figure 4:
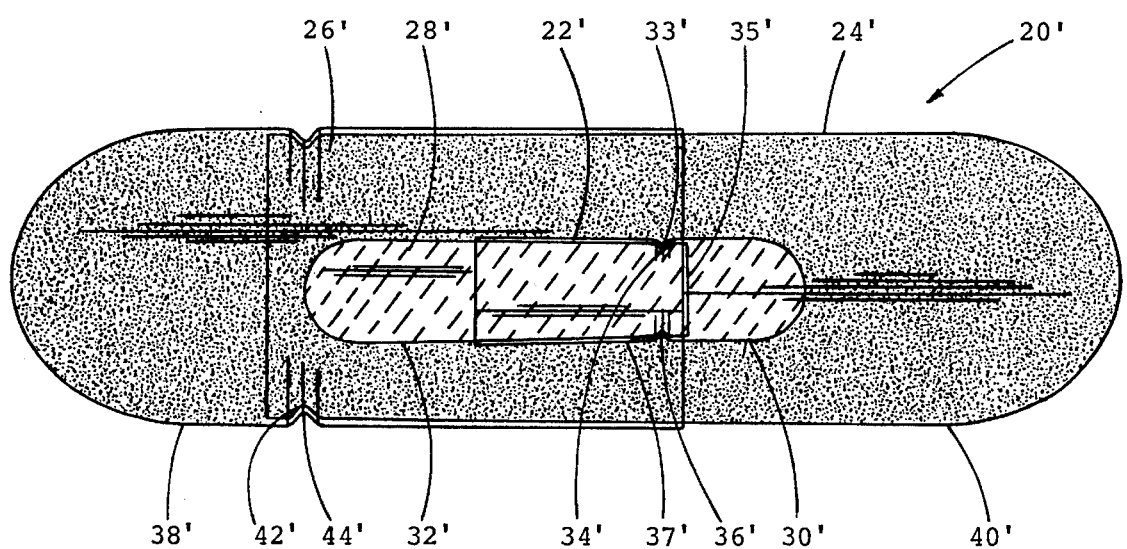
FIG. 4 shows an enlarged sectional view of the capsule-in-a-capsule structure in accordance with the present invention, with the microorganisms outside of the inner capsule and with the vitamins and/or minerals admixture in the inner capsule.
Figure 5E:
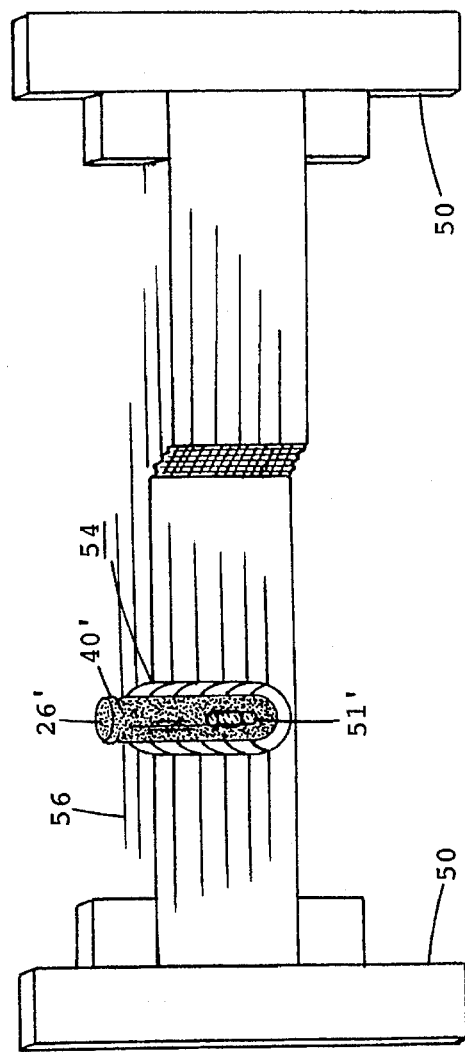
Figure 5F:
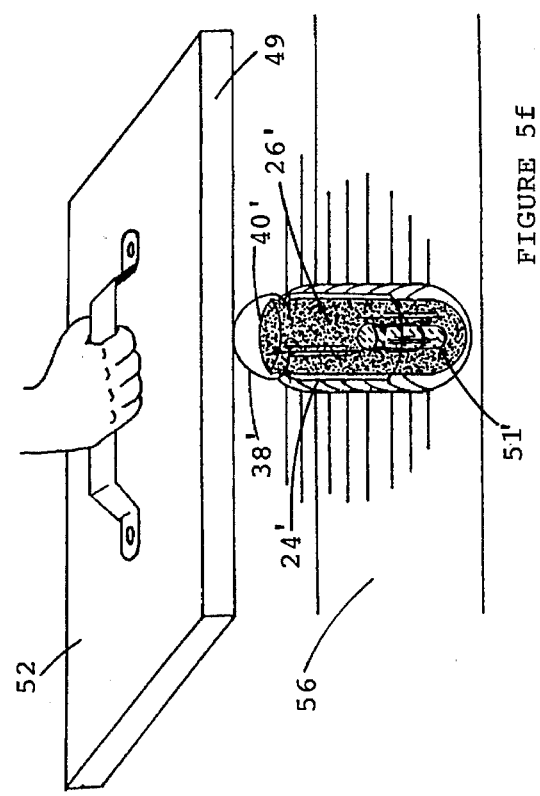

FIG. 1 illustrates a capsule-in-a-capsule structure in accordance with the present invention and is generally designated as 20. Capsule-in-a-capsule 20 includes an inner capsule 22 and an outer capsule 24. The inner capsule 22 is within the outer capsule 24. Inner capsule 22 contains viable microorganisms 26 and outer capsule 24 contains vitamins and/or minerals generally designated as 28. Inner capsule 22 includes a top member 30 and a bottom member 32 which is bigger than top member 30. Top member 30 and bottom member 32 are locked together after filling by a locking mechanism 33 which includes a groove 34 proximate the top 35 of bottom portion 32 and a complementary ridge 36 substantially about the mid-portion 37 of top portion 30, forming a circumferentially nested ridge and groove. Similarly, outer capsule 24 has a top member 38 and a bottom member 40 in which top member 38 is locked to bottom member 40 with a groove 42 and a ridge 44. Alternatively the content of the inner and outer capsules may be reversed as is shown in FIG. 4 and wherein the capsule-in-a-capsule vehicle 20' is depicted with microorganisms 26' contained within the outer capsule and with the vitamin and/or mineral admixture 28' contained in the inner capsule. FIG. 4 illustrates a capsule-in-a-capsule structure in accordance with the present invention and is generally designated as 20'. Capsule-in-a-capsule 20' includes an inner capsule 22' and an outer capsule 24'. The inner capsule 22' is within the outer capsule 24'. Inner capsule 22' contains vitamins and/or minerals generally designated as 28' and outer capsule 24' contains viable microorganisms 26'. Inner capsule 22' includes a top member 30' and a bottom member 32' which is bigger than top member 30'. Top member 30' and bottom member 32' are locked together after filling by a locking mechanism 33' which includes a groove 34' proximate the top 35' of bottom portion 32' and a complementary ridge 36' substantially about the mid-portion 37' of top portion 30', forming a circumferentially nested ridge and groove. Similarly, outer capsule 24' has a top member 38' and a bottom member 40' in which top member 38' is locked to bottom member 40' with a groove 42' and a ridge 44'.

The capsules, in either FIG. 1 or FIG. 4, are preferably made of gelatin, however other materials which dissolve in the animal's gastrointestinal system, as are known in the art, may also be used and are encompassed by the invention. Capsule shells are, however, easily reformulated to meet a myriad of size, transportation, storage, and administration requirements, e.g., excessive heat or cold, vibration, humidity, compression or impact, aeration, or ultraviolet light. The shell of the inner capsule forms a wall, separating the contents contained within the inner capsule from the substance external to the inner capsule, but contained within the outer capsule.

In structure 20, the microorganisms 26 of the first component, i.e., of inner capsule 22, include one or more of the indigenous gastrointestinal bacteria selected from *Lactobacillus acidophilus, Lactobacillus lactis, Lactobacillus casei, Streptococcus faecium*, and *Pediococcus cerevisiae* and/or microorganisms including the live cell yeast *Saccharomyces cerevisiae*, fungus *Aspergillus oryzae*, and/or bacteria Bifidobacterium and Propionibacterium. All of these microbes are publicly available from commercial sources such as Far-Mor Biochem, Milwaukee, Wis. Chr. Hansen's Laboratory, Inc., Milwaukee, Wis. Red Star® Yeast Products, Milwaukee, Wis. and Agtech Products, Inc., Waukesha, Wis. By live cell yeast culture is meant, a yeast culture containing live yeast cells but not containing yeast metabolites and/or the yeast growth media. The microorganisms can be processed in accordance with conventional methods of bacteriology to produce direct-fed microbial agents suitable for encapsulation in gelatin-shelled capsules and administration to cattle, sheep and goats, and ratites. The in vitro viability of the microorganisms of the inner capsule is determined by counting the colony-forming units per gram (CFU/g) of the culture administered, according to standard feed industry protocols such as those developed by the American Feed Ingredients Association (AFIA) or the National Feed Ingredients Association (NFIA). At time of preparation, the microbial count in the inner capsule in accordance with the present invention depends upon the microorganism used and is suitably about $20 \times 10^9$ CFU/g for *Lactobacillus acidophilus, Lactobacillus lactis, Lactobacillus casei, Streptococcus faecium*, and *Pediococcus cerevisiae*; about $10 \times 10^9$ CFU/g for live cell yeast Saccharomyces cerevisiae; about $1 \times 10^7$ CFU/g for *Asperigillus oryzae*; about $20 \times 10^9$ CFU/g for Bifidobacterium; and about $2 \times 10^{11}$ CFU/g for Propionibacterium. As is known in the art, the invention comprehends the use of the standard formulation overages for determining the amount of microbial culture present. The standard overage depends on the culture used and ranges typically from 0 to 50%. For example for the lactic acid producing bacteria an overage of 50% is typical, for yeasts 50%, for Bifidobacterium 50% for Propionibacterium 50%, and for *Asperigillus oryzae* about 0%.

The microorganisms can be employed in admixtures with conventional excipients, e.g., acceptable feed grade carriers suitable for enteral (e.g. oral) administration which do not deleteriously react with the microorganisms. By the term "deleteriously react" it is meant that the feed grade carrier does not inhibit, or prevent growth or diminish the viability of the microorganisms. Suitable feed grade carriers include, but are not limited to, calcium carbonate, nonhygroscopic whey, rice hulls, and sucrose.

The microbial preparations can also be mixed with auxiliary agents, e.g., whole dried milk, dextrose, enzymes, plasma proteins or amino acids to promote the growth and nutritional status of the animal and the microbials in vivo.

The vitamins and minerals of the second component, i.e., outer capsule, are selected from one or more vitamins, namely, A, $B_{12}$, C, D, E, and K, niacin, thiamine, choline, biotin, folic acid, riboflavin, pantothenic acid, and/or one or more minerals, namely, cobalt, copper, iron, manganese, selenium and zinc.

The vitamins and/or minerals of the outer capsule 28 can be processed in accordance with conventional methods of pharmacy to produce agents suitable for encapsulation in gelatin-shelled capsules and administration to cattle, sheep, goats, and ratites. For example, the vitamins and minerals can be administered in alternative sulfate, oxide, chelated, or other chemical forms to promote efficient dissolution and absorption in vivo.

The vitamins and/or minerals can also be employed in admixtures with conventional excipients, e.g., acceptable feed grade carriers which do not deleteriously react with them. Suitable carriers include, but are not limited to, antioxidants, cellulose, grain by-products, or other inert vegetable materials. Nutrient-rich, dried organic materials, such as kelp, are highly preferred carrier materials, as they contribute significantly to the vitamin and mineral status of the animal and gastrointestinal microorganisms, including but not limited to the rumen and/or intestinal microorganisms.

Alternatively, the locations of the aforementioned microorganisms and the vitamin and/or mineral admixture is reversed as is disclosed in FIG. 4.

It should be noted that for certain applications, as are disclosed in the following Examples 1–17 and 23, the capsule-in-a-capsule vehicles for adult cattle are suitably prepared in 15–20 g double capsules and capsule-in-a-capsules for calves are suitably prepared as 4.5–6 g double capsules. The variable weights depend upon the density of the components. Both sizes of capsules are orally administered daily as 1–2 capsule-in-a-capsule vehicles for three consecutive days at parturition or other signs of stress or feed distress.

As best described in the following Examples 22 and 21, for emus and ostriches on corn and grain rations, the capsule-in-a-capsule vehicles are suitably prepared in 6 g double capsules, and for emus and ostriches on alfalfa and forage based rations, the capsule-in-a-capsule vehicles are suitably prepared in 2.5 g double capsules. For Examples 21 and 22, one (1) to two (2) capsule-in-a-capsule vehicles are administered orally daily for three consecutive days at sign of stress or feed distress.

It will be appreciated, however, that the actual preferred amounts of the compounds/substances in the inner and outer capsules will vary according to the age, weight and species of animal being treated, and the particular feeding disorder of interest. For example, the amounts of vitamins and minerals in outer capsules for calves are suitably one-third of that in outer capsules for adult cattle for certain applications. Feed guidelines can be determined by means of an appropriate conventional dietary protocol.

In another embodiment, the invention provides a method for simultaneously delivering incompatible substances to livestock in vivo. Specifically, the method includes oral administration of a capsule-in-a-capsule which structure includes a first gelatin-shelled capsule containing a first substance and a second gelatin-shelled capsule encapsulating the first capsule that contains a substance incompatible with the first. When the first substance is a bacterial culture of gastrointestinal microorganisms, *Lactobacillus acidophilus, Lactobacillus lactis, Lactobacillus casei, Streptococcus faecium*, and *Pediococcus cerevisiae*, such method delivers at least $3 \times 10^9$ CFU/capsule-in-a-capsule.

The method in accordance with the present invention advantageously preserves the activity of mutually reactive or otherwise incompatible substances by physically separating them during production, storage and administration. When live microorganisms are stored and administered to animals simultaneously with vitamins and minerals in bolus or single capsule formulations, the microorganisms often are rendered nonviable before administration. The present method advantageously facilitates the consolidation of multi-step therapies into easily administered, single-step therapies. Such efficient administration eliminates the stresses induced by the sequential administration of multi-phase treatment components and ensures the delivery of correct unit doses. The capsule-in-a-capsule vehicle is suitably delivered by hand or balling gun to cattle, sheep, goats, ostriches and emus, among others.

In another aspect, the invention is an oral nutritional supplement delivery system for livestock. The system is a two-component system which effects near simultaneously delivery of the two components. The system comprises a first capsule containing at least one live microorganism and a second capsule enclosing both the first capsule and an admixture of vitamins and/or minerals, incompatible with live microorganisms. Alternatively, the first capsule contains the admixture of vitamins and/or minerals and the second capsule encloses both the first capsule and contains at least one type of live gastrointestinal microorganisms. The capsules physically separate the incompatible nutrient supplements from the microorganism cultures, thereby eliminating the need for separate administration of the microorganisms and the vitamin and/or mineral admixture. The size of the capsule used is determined in part by relative volume, i.e., number of grams of the two substances to be fed.

To fabricate a capsule-in-a-capsule in accordance with the present invention, a first capsule, typically a gelatin capsule, is filled with a first substance and capped. This first capsule is placed inside the bottom member of a second, larger capsule, typically also a gelatin capsule, and the second capsule is then filled with a second substance, incompatible with the first substance, and capped. If the first substance is the microorganisms, then the second substance is the vitamin and/or mineral admixture, (FIG. 1). Alternatively, if the first substance is the vitamin and/or mineral admixture, then the second substance is the microorganisms, (FIG. 4). This method for efficiently and inexpensively preparing a shelf-stable composition of incompatible substances constitutes another aspect of the invention. The steps may be performed manually or by machine. This method of fabrication has certain production economics compared to production of hard boluses.

Capsule-in-a-capsules can also be fabricated by machine using, e.g., a Torpac Capsule Filling Machine commercially available (Torpac, Ltd. East Hanover, N.J.).

Reference is now made to FIGS. 2a–2f which illustrate a method of preparing the capsule-in-a-capsule formulation of the present invention best shown in FIG. 1 where the first substance is the microorganism, i.e., microbial, and the second substance is the vitamin and/or mineral admixture. Specifically, the larger bottom members 32 of the inner, smaller capsules 22 are first placed in openings 46 in an assembly board 48 in a housing 50. Each bottom shell 32 is then filled with the microorganisms i.e., direct-fed (probiotic) microbial culture 26. Top member 30 is then placed on each bottom member 32 and "locked" in place by using a mechanism which is the same or similar to locking mechanism 33 described hereinbefore by gentle pressure from pressboard 49 to form a sealed capsule 51. Filled sealed capsules 51 are ejected from the board 48, and the board 48 is removed from the housing 50.

A second assembly board 56, having holes 54, corresponding to the bottom members 40 of larger capsules 24, is placed in the machine housing 50. The bottom members 40 of the larger capsules 24 are placed in the board 56, and one sealed capsule 51 containing the microorganisms is placed within each. The remaining volume of each bottom member 40 of capsule 24 is then filled with the second substance, the vitamin and/or mineral admixture 28. A top member 38 is then placed over each bottom member 40 and locked as described previously in place with gentle pressure from the pressboard 52. The resulting capsule-in-a-capsule is then ejected from the second board 56.

This same method of preparing the capsule-in-a-capsule formulation is used to prepare the alternate embodiment (FIG. 4), where the first substance within the inner capsule is the vitamin and/or mineral admixture and where the second substance is the microorganism, i.e., microbial.

Reference is now made to FIGS. 5a–5f which illustrate a method of preparing the capsule-in-a-capsule 20' formulation of the present invention shown in FIG. 4 where the first substance is the vitamin and/or mineral admixture 28' and the second substance is the microorganism 26', i.e, probiotic or microbial culture Specifically, like numbers are used to correspond to similar parts as discussed for FIG. 1. The larger bottom members 32' of the inner, smaller capsules 22' are first placed in openings 46 in an assembly board 48 in a housing 50. Each bottom shell 32' is then filled with the vitamin and/or mineral admixture 28'. Top member 30' is then placed on each bottom member 32' and "locked" in place by using a mechanism which is the same or similar to locking mechanism 33 described hereinbefore by gentle pressure from pressboard 49 to form a sealed capsule 51'. Filled sealed capsules 51' are ejected from the board 48, and the board 48 is removed from the housing 50.

A second assembly board 56, having holes 54, corresponding to the bottom members 40' of larger capsules 24', is placed in the machine housing 50. The bottom members 40' of the larger capsules 24' are placed in the board 56, and one sealed capsule 51' containing the vitamin and/or mineral admixture is placed within each. The remaining volume of each bottom member 40' of capsule 24' is then filled with the microorganisms, i.e., microbial culture 26'. A top member 38' is then placed over each bottom member 40' and locked as described previously in place with gentle pressure from the pressboard 52. The resulting capsule-in-a-capsule is then ejected from the second board 56.

This fabrication method can be used to produce significantly more stable probiotics, as shown in FIGS. 1 and 4, than conventional bolus or single-capsule delivery systems which combine sensitive microorganisms with toxic concentrations of vitamins and/or trace minerals. The use of a multiple capsule also facilitates the administration of higher, more efficacious doses of vitamins and minerals than are delivered by conventional boluses. Further, gelatin-shelled capsules are efficiently and inexpensively assembled, thereby incurring reduced production costs relative to microencapsulation or hard bolus vehicles. The contents of such capsules also are not subjected to extremes of temperature, pressure or abrasion during their manufacture, thereby facilitating the consolidation of multi-step therapies utilizing components sensitive to such conditions.

Finally, capsule shells which are easily reformulated to provide particular protection to enclosed materials (e.g., different sized capsules or ultra-violet light filtering capsules) may be used interchangeably and in concert with other capsule shells of standard feed grade composition° In contrast, microencapsulation equipment cannot accommodate frequent coat or nutrient composition reformulations without costly equipment changes.

The present invention is further explained by way of the following examples which are to be construed as merely illustrative, and not limitative, of the remainder of the disclosure in any way whatsoever. In the following examples, all temperatures are expressed in degrees Celsius. All test capsules were randomly selected for analysis, and microorganisms were enumerated using the American Feed Ingredient Association's Standard Practice for the Enumeration of Microorganisms from Direct-Fed Microbials and Silage Innoculants. Microbial viability is expressed in colony-forming units per gram of source material (CFU/g) or CFU per capsule, or depending upon the application, CFU per bolus. In the following Examples, the capsules are typically made of gelatin, unless otherwise noted. The capsule-in-a-capsule vehicles of Examples 1, 7–12 and 20–24 are structurally configured as shown in FIG. 1. The capsule-in-a-capsule vehicles of Examples 13–19 and 25 are structurally configured as shown in FIG. 4.

EXAMPLE 1

Preparation of Capsule-in-a-Capsule with Rumen Intestinal Bacteria as Probiotic

Capsule-in-a-capsule vehicles appropriate for administration to adult cattle were prepared by the method as described hereinbefore with the rumen intestinal bacteria in the innermost gelatin capsule. The bacterial cultures were commercial formulations of dormant *Lactobacillus acidophilus, Lactobacillus lactis, Lactobacillus casei, Streptococcus faecium,* and *Pediococcus cerevisiae* having a viability of $20.0 \times 10^9$ CFU/g at the time of preparation. The vitamin and mineral admixture was contained in the outermost capsule and contained the following in the amounts indicated in parentheses: vitamin A ($5 \times 10^5$ IU), vitamin D ($7.5 \times 10^4$ IU), vitamin E (750 IU), vitamin $B_{12}$ (2000 mcg), niacin (3000 mg), pantothenic acid (15 mg), choline (750 mg), biotin (75 mcg), cobalt (20 mg), copper (none), iron (30 mg), manganese (30 mg), zinc (75 mg), and trace quantities of riboflavin, thiamine, folic acid, vitamin K, vitamin C, and selenium. The unit mcg is microgram and the unit mg is milligram. Each capsule-in-a-capsule contained approximately 0.25 g of bacterial culture and 12.5 g of the vitamin and mineral admixture, the above-enumerated vitamins and minerals having been combined with kelp, an acceptable and nutrient-rich feed grade carrier.

Capsule-in-a-capsule vehicles appropriate for administration to calves were prepared by an identical method, excepting that the vitamin and mineral admixture contained approximately one-third of the amounts of the vitamins and minerals enumerated above for use in the adult cattle capsule-in-a-capsules. Each calf-size capsule-in-a-capsule contained approximately 0.25 g of bacteria culture and 3.5 g of the vitamin and mineral admixture, the vitamins and minerals having also been combined with kelp. Capsule-in-a-capsule vehicles identical to those of Example 1 were used in the following tests where indicated.

EXAMPLE 2

Determination of the Efficacy of Capsule-In-A-Capsule for Preserving the Viability of Anaerobic Bacterial Colony Forming Units Capsule-in-a-capsule vehicles appropriate for administration to adult cattle as described in Example 1 were variously tested against single capsule forms with an admixture of cultures and nutrient supplements as used in the adult cattle capsule-in-a-capsule form. All capsules were stored at room temperature for one week following their preparation. The capsule-in-a-capsules were randomly apportioned to two experimental groups, A and B. Each had 0.25 g microbials and 12.5 g vitamin and mineral admixture. The single capsules enclosing admixed microbes and nutrient supplements comprised group C, and group D (control) comprised an unencapsulated sample of the microbial culture. The theoretical microbial activity was $23 \times 10^9$ CFU per g of microbes. The inner capsule of a single group A sample contained, therefore, about $5.75 \times 10^9$ CFU total, since each inner capsule contains 0.25 g. The bacteria content of a single group C capsule was about $5.75 \times 10^9$ CFU.

Inner capsule contents of four group A samples (1 gram total), outer capsule contents of one group B sample (12.5 g vitamin and mineral admixture), capsule contents of one group C sample (0.25 g microbes plus 12.25 g vitamin and mineral admixture for 12.5 g total), group D control culture (microbes only) were randomly selected for comparison. Each test sample was individually serially diluted in autoclaved 6.25 mM phosphate buffer at pH=7.2. One (1) ml aliquots of each dilution were transferred into separate sterile petri plates. Twenty (20) ml of sterile LMRS (Lactobacilli Man Rugosa Sharpe Agar), cooled to 44° C. to 46° C., were then added to each petri plate with swirling. The plates were covered and cooled to room temperature before being inverted and placed into GasPak™ anaerobic jars. The plates were incubated at 35° C. until colonies were readily discernable, approximately two to three days. Colonies were then counted using a Quebec colony counter.

These data and the bacterial survival rate are given in Table 1 below.

TABLE 1

Bacterial Viability of Capsule-In-A-Capsule

| Test Group | Theoretical Bacterial Count At Preparation, CFU/g of Sample Tested | Bacterial Count, CFU/g of Sample, 1 Week After Preparation | Bacteria Survival, % |
| --- | --- | --- | --- |
| A | $23 \times 10^9$ | $23 \times 10^9$ | 100 |
| B | — | $6 \times 10^2$ | — |
| C | $4.6 \times 10^8$ | $<10^6$ | <.21 |
| D (control) | $23 \times 10^9$ | $23 \times 10^9$ | 100 |

These data indicate that the contents of intact, gelatin-shelled capsule-in-a-capsules successfully retain 100% of their colony-forming activity after one week of storage at room temperature. Conversely, capsules which do not separate microbial cultures from nutrient supplement materials are not successful in protecting bacterial viability, and their contents lose 99.79% of their colony-forming activity within one week.

EXAMPLE 3

Determination of the Shelf Stability of Anaerobic Bacterial Colony Forming Units Packaged in Capsule-In-A-Capsules During Long-Term Storage at Room Temperature Capsule-in-a-capsules suitable for administration to adult cattle were fabricated as described above in Example 1 and stored at room temperature. At preselected intervals after their manufacture, i.e, one, two, three, four, five and six months, inner capsules containing the bacterial cultures were removed from randomly selected capsule-in-a-capsules. The contents of each inner capsule were serially diluted in autoclaved 6.25 mM phosphate buffer, pH=7.2, and 1 ml aliquots of each dilution were transferred into sterile petri plates. Twenty (20) ml of sterile LMRS Agar cooled to 44° C. to 46° C. were then added to each petri plate with swirling. The plates were covered and cooled to room temperature before being inverted and placed into GasPak™ anaerobic jars. The plates were incubated at 35° C. until colonies were readily discernable, approximately two to three days. Colonies were then counted using a Quebec colony counter. These data and the bacterial survival rates are given in Table 2 below. Initial bacterial count was $22.5 \times 10^9$ CFU/g.

TABLE 2

Shelf Stability of Capsule-In-A-Capsule

| Time After Manufacture, mos. | Bacterial Count, CFU/g | Bacterial Survival, % |
| --- | --- | --- |
| 0 | $22.5 \times 10^9$ | |
| 1 | $22.5 \times 10^9$ | 100 |
| 2 | $20.0 \times 10^9$ | 89 |
| 3 | $21.2 \times 10^9$ | 94 |
| 4 | $16.1 \times 10^9$ | 72 |
| 5 | $13.0 \times 10^9$ | 58 |
| 6 | $12.0 \times 10^9$ | 53 |

These data indicate that sufficient bacteria remain viable in the capsule-in-a-capsule vehicle to repopulate the gastrointestinal tract after six months of storage under typical field conditions. In contrast, the Percentage Bacterial Survival of conventional boluses approaches zero approximately four weeks after manufacture under similar conditions as shown in Table 3 of Example 4.

EXAMPLE 4

Determination of the Shelf Stability of Anaerobic Bacterial Colony Forming Units Combined with Vitamin and Mineral Supplements During Long-Term Storage at Room Temperature The shelf stability of single capsule formulations identical to the adult cattle capsule-in-a-capsule formulations of Example 1 were determined. Single gelatin-shelled capsules were filled with an admixture of the bacterial culture and vitamin and mineral supplement in a 1:39.55 gram:gram ratio present in the capsule-in-a-capsule vehicle of Example 1. The capsules were packed in ice for two days prior to testing; thereafter all capsules were stored at room temperature. A pure sample of the microbial culture was reserved on ice as a control.

At 2, 3, 4, 5, 8, 12, 16, 20, 25, and 32 days after manufacture, the contents of three randomly-selected capsules were nonabrasively combined, and samples therefrom were serially diluted in autoclaved 6.25 mM phosphate buffer at pH=7.2. During the initial analysis, a control sample from the microbial culture control was also diluted and analyzed. One (1) ml aliquots of each dilution were transferred in duplicate into separate sterile petri plates. Twenty (20) ml of sterile Lactobacillus MRS Agar, cooled to 44° C. to 46° C., were then added to each petri plate with swirling. The plates were covered and cooled to room temperature before being inverted and placed into GasPak™ anaerobic jars. The plates were incubated at 35° C. until colonies were readily discernable, approximately two to three days. Colonies were then counted using a Quebec colony counter.

These data and bacterial survival rates are given in Table 3 below. Initial bacterial count was calculated as $37 \times 10^7$ CFU/g.

TABLE 3

Shelf Stability of Single Capsules Equivalent to Capsule-In-A-Capsule

| Time After Manufacture, days | Bacterial Count, CFU/g | Bacterial Survival, % |
|---|---|---|
| 2 | $21.0 \times 10^7$ | 56.7 |
| 3 | $4.5 \times 10^7$ | 12.1 |
| 4 | $10.0 \times 10^7$ | 27.0 |
| 5 | $119 \times 10^7$* | >100 |
| 8 | $10.0 \times 10^7$ | 27.0 |
| 12 | $15.0 \times 10^7$ | 40.5 |
| 16 | $4.2 \times 10^7$ | 11.3 |
| 20 | $3.1 \times 10^7$ | 8.3 |
| 25 | $2.6 \times 10^7$ | 7.0 |
| 32 | $0.27 \times 10^7$ | 0.7 |

*possible counting error

These data demonstrate that bacteria packaged directly with nutrient supplements lose nearly 50% of their colony-forming activity within two days of manufacture and nearly 100% of their colony-forming activity within 33 days of manufacture. Thus, the physical separation of the microbes and nutrients effected by the multiple capsule vehicle is responsible for the superior delivery of viable microbes after long-term storage demonstrated in Example 3.

EXAMPLE 5

Comparison of Anaerobic Bacterial Colony Forming Units Per Gram of Hard Bolus and Capsule-In-A-Capsule within their Expiration Period Bacterial viability of capsule-in-a-capsules in accordance with the present invention were compared with various commercially available hard boluses purporting to contain similar microorganisms and vitamins and minerals. The following products were tested and compared to the capsule-in-a-capsule formulation of the present invention (both adult cattle and calf-size formulations were tested):

| Product No. | Number of Boluses Used to Make a 22 Gram Sample | Product Description/Name |
|---|---|---|
| (cow size) | | |
| 01 | 2 | Present Invention (capsule-in-a-capsule) |
| 02 | 2 | Primilac™ Cattle bolus, Star Labs |
| 03 | 2 | Probiocin™ Bolus, Pioneer Hi-Bred International, Inc. |
| 04 | 1 | T.N.T. Stress Bolus, Tomorrow's Nutrition Today |
| (calf size) | | |
| 05 | 5 | Present Invention (capsule-in-a-capsule) |
| 06 | 4 | Equal-lizer, Med-Vet Pharma |
| 07 | 5 | Lactobols™, United Agri-Sales |
| 08 | 4 | LactoPlus™, Vet's Plus |
| 09 | 4 | LBA™, Osborn/Int'l Multifoods |
| 10 | 4 | Problocin™, Pioneer Hi-Bred International, Inc. |
| 11 | 4 | T.N.T. Stress Bolus, Tomorrow's Nutrition Today |

The above-described number of samples of each commercial bolus and capsule-in-a-capsule as described in Example 1 product were randomly selected from commercial shipments within their expiration periods. Boluses from each commercial brand were individually ground with a sterile mortar and pestle and then combined with the others of this brand. Each capsule-in-a-capsule was manually disassembled and the contents thereof combined with those of other disassembled capsule-in-a-capsules.

Twenty-two gram portions of each ground bolus mixture or disassembled capsule-in-a-capsule mixture, and 450 ml of sterile 6 mM phosphate buffer, pH=7.2, were blended for 1 min at low speed in a sterile stomacher bag. Each mixture was then serially diluted in additional phosphate buffer. Each dilution was plated in triplicate by placing a 1 ml aliquot in each of three sterile petri plates and adding 15 ml of 44°–46° C. MRS (Man Rugosa Sharpe) Agar to each plate with swirling. The plating procedure was then replicated for each dilution using LBS (Lactobacilli Sharpe) Agar and then MRSO (Man Rugosa Sharpe with 0.15% Oxgall) Agar. The plates were covered and cooled to room temperature, at which time 4 ml of 44°–46° C. tempered agar were applied to the plate surface. After the tempered agar solidified, the plates were inverted and placed in anaerobic jars for incubation at 32° C. for 72 hrs. Colonies on each plate were then counted according to standard methods.

The above-described procedure was repeated for a second, identically selected group of capsule-in-a-capsules, and the results of both studies were averaged to describe the colony-forming potential delivered by each vehicle. The results are graphed in FIG. 3. Activity on MRS agar reflects the total activity attributable to anaerobic lactic acid producing bacteria, the type of bacteria which the vehicles are intended to deliver while activity on LBS agar reflects the total activity attributable to lactobacillus type lactic acid producing bacteria. Activity on MRSO agar reflects the total activity of intestinal anaerobic lactic acid producing bacteria, as the added Oxgall inhibits all but bile-resistant species.

Figure 3:
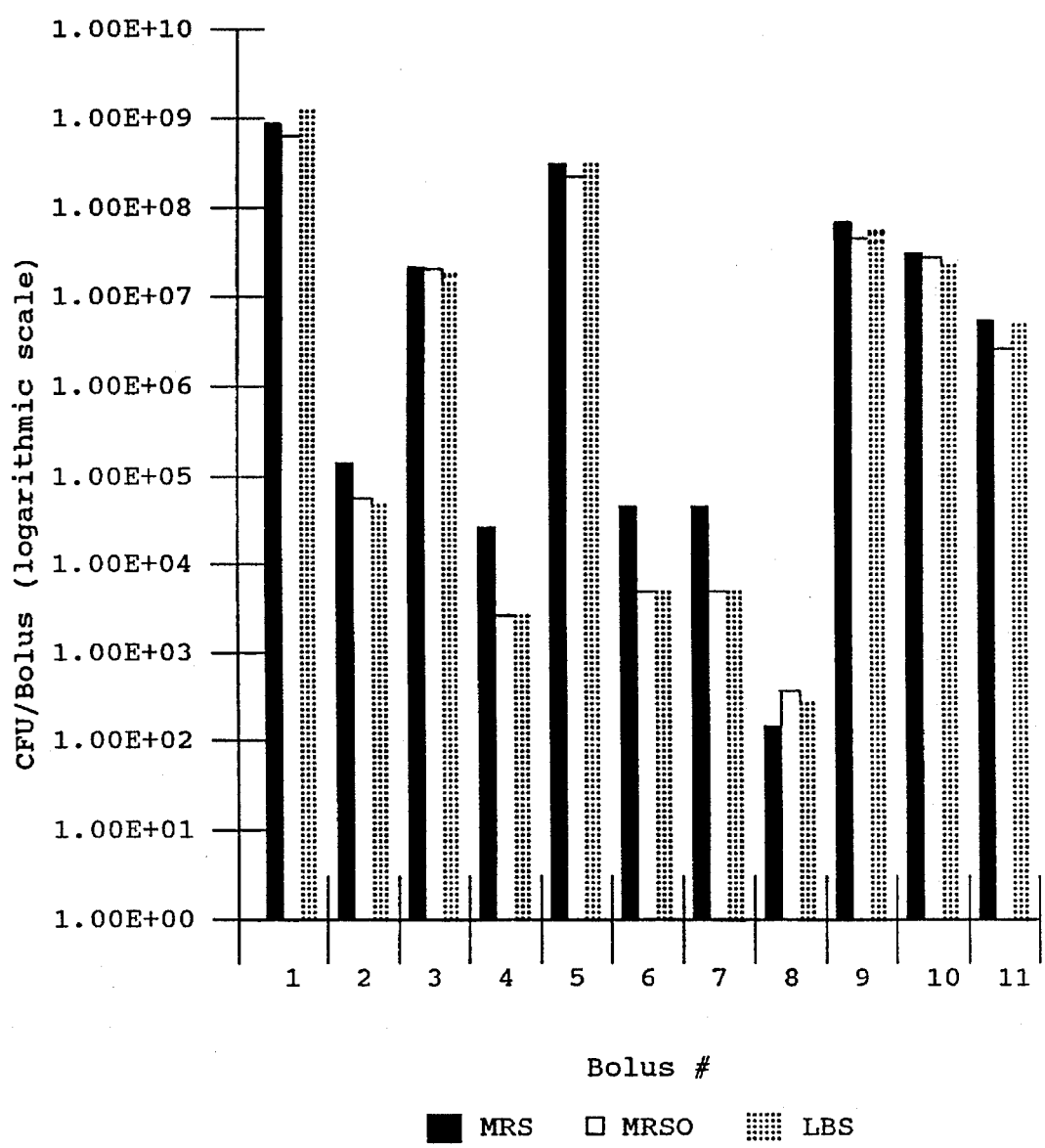
FIG. 3 compares the efficacy of double capsules in accordance with the present invention and hard boluses in simultaneously delivering live microorganisms and incompatible nutrient supplements.

These data illustrated in FIG. 3 indicate that use of the capsule-in-a-capsule delivery system facilitates the delivery of 13 times to 54 million times more lactic acid producing bacteria CFU/Bolus than conventional hard boluses. These data further indicate that a minimum of 92% of the viable bacteria are the desired lactobacilli, and between 60 and 67% of those bacteria are bile-resistant species presumably capable of successfully repopulating the intestine.

EXAMPLE 6

Comparison of Capsule-In-A-Capsule and Standard Hard Bolus Dissolution Times in vivo Dissolution times in vivo for capsule-in-a-capsules in accordance with the present invention as described in Example 1 and commercially available hard bolus formulations were compared. Both adult cattle and calf-size formulations were tested. Randomly selected, intact capsule-in-a-capsules and the commercially available hard boluses of Example 5 were placed in nylon floss slings and lowered into separate 500 ml erlenmeyer flasks of fresh cow rumen contents. The flasks were maintained at 101.5° F. and a pH=6.35, without stirring. Samples were raised from the fluid for examination at regular intervals until complete dissolution was achieved, thereby establishing approximate dissolution times for each.

After the approximate dissolution times were established, a second sample of capsule-in-a-capsules and hard boluses were randomly selected from the groups of Example 5, placed in slings, and lowered into 500 ml erlenmeyer flasks of fresh cow rumen contents. These flasks were maintained at the above-described temperature and pH. Individual samples were examined at intervals ranging from 30 sec. to 30 min., according to the dissolution times previously established. Flask contents were examined to confirm complete dissolution when empty slings were observed. The dissolution times are given in Table 4.

TABLE 4

Comparison of Dissolution Times of Capsule-In-A-Capsule and Hard Boluses

| Product Number | Dissolution Time Trial 1 | Trial 2 | Average Time, sec. | Average Time, min. |
| --- | --- | --- | --- | --- |
| (cow size) | | | | |
| 01 (present invention) | 410 | 531 | 470.5 | 7.84 |
| 02 | 12720 | 12780 | 12750 | 212.50 |
| 03 | 2144 | 2170 | 2157 | 35.95 |
| 04 | 2227 | 2286 | 2256.5 | 37.61 |
| (calf size) | | | | |
| 05 (present invention) | 323 | 372 | 347.5 | 5.79 |
| 06 | 3632 | 5423 | 4527.5 | 75.46 |
| 07 | 10620 | 10680 | 10650 | 177.00 |
| 08 | 19380 | 22020 | 20700 | 345.00 |
| 09 | 22020 | 23160 | 22590 | 376.50 |
| 10 | 2472 | 2503 | 2487.5 | 41.46 |
| 11 | 2530 | 2549 | 2539.5 | 42.33 |

Average dissolution times of both capsule-in-a-capsule test samples ranged from 5.79 to 7.84 min. for the gelatin-shelled capsule-in-a-capsules, while average dissolution times for the hard boluses ranged from 36 to 76 min. These data indicate that nutritional compositions delivered via capsule-in-a-capsule vehicles are virtually immediately available to distressed animals, while hard bolus contents may not become available for an extended period of time.

EXAMPLE 7

Preparation of Capsule-in-a-Capsule With Gastrointestinal Lactic Acid Producing Bacteria as the Probiotic Capsule-in-a-capsule vehicles appropriate for administration to adult cattle were prepared by the method as described hereinbefore with the gastrointestinal lactic acid producing bacteria in the inner gelatin capsule. The probiotic bacterial culture was a formulation of dormant commercially available cultures of the lactic acid producing bacteria *Lactobacillus acidophilus, Lactobacillus lactis, Lactobacillus casei, Streptococcus faecium* and *Pediococcus cerevisiae*, (available from Agtech Products, Inc., Waukesha, Wis.; FarMor Biochem, Milwaukee, Wis.) having a viability of $20 \times 10^9$ CFU/g at the time of preparation. Capsule-in-a-capsule vehicles appropriate for administration to adult cattle contained bacterial levels of $3 \times 10^9$ CFU per capsule. The outer capsule contained the inner capsule and the vitamin and/or mineral admixture. The vitamin and mineral admixture contained the following amounts per capsule as indicated in parentheses: vitamin A ($5 \times 10^5$ IU), vitamin $D_3$ ($7.5 \times 10^4$ IU), vitamin E (750 IU), vitamin B12 (2,000 mcg), niacin (3,000 mg), pantothenic acid (15 mg), choline (750 mg), biotin (75 mcg), cobalt (3 mg), copper (15 mg), iron (30 mg), manganese (30 mg), zinc (75 mg) and trace quantities of riboflavin, thiamine, folic acid, vitamin K, vitamin C and selenium.

Each cattle size capsule-in-a-capsule contained approximately 0.25 g of bacterial culture (including standard formulation overages), and 12.5 g of the vitamin and mineral admixture. The above enumerated vitamin and mineral admixture was preferably combined with kelp, an acceptable and nutrient-rich feed grade carrier.

Capsule-in-a-capsule vehicles appropriate for administration to calves were prepared by an identical method, except that the vitamin and/or mineral admixture contained approximately one-third of the amounts of the vitamins and minerals enumerated above for use in the adult cattle capsule-in-a-capsules. The vitamin and mineral levels per capsule-in-a-capsule were as follows: vitamin A ($1.65 \times 10^5$ IU), vitamin $D_3$ ($2.5 \times 10^4$ IU), vitamin E (250 IU), vitamin B12 (650 mcg), niacin (1,000 mg), pantothenic acid (5 mg), choline (250 mg), biotin (25 mcg), cobalt (1 mg), copper (5 mg), iron (10 mg), manganese (10 mg), zinc (25 mg) and trace quantities of riboflavin, thiamine, folic acid, vitamin K, vitamin C and selenium. Capsule-in-a-capsule vehicles appropriate for administration to calves contained bacterial levels of $3 \times 10^9$ CFU per capsule.

Each calf size capsule-in-a-capsule contained approximately 0.25 g of bacterial culture (including standard formulation overages), and 3.5 g of the vitamin and mineral admixture, the vitamins and minerals having also preferably been combined with kelp, an acceptable and nutrient-rich feed grade carrier. The outer gelatin capsule enclosed the inner capsule. The vitamin and/or mineral admixture was outside the inner capsule and was enclosed in the outer capsule.

EXAMPLE 8

Preparation of Capsule-in-a-Capsule With the Probiotic Saccharomyces Cerevisiae (live cell culture)

Capsule-in-a-capsule vehicles appropriate for administration to adult cattle are prepared by the method as described hereinbefore with the inner gelatin capsule containing the microorganisms, i.e., the yeast. The microbial probiotic culture is a formulation of commercially available dormant live cell *Saccharomyces cerevisiae*, (ADY-20, available from Red Star Yeast Products, Milwaukee, Wis.) having a viability of $10\times10^9$ CFU/g at the time of preparation.

The outer capsule contains the inner capsule and the vitamin and/or mineral admixture. Each capsule-in-a-capsule contains 5 g of live cell *Saccharomyces cerevisiae* culture (including standard formulation overages), and 6 g of vitamin and mineral admixture. The vitamin and mineral admixture contains the following amounts per capsule as indicated in parentheses: vitamin A ($2.8\times10^5$ IU), vitamin $D_3$ ($4.2\times10^4$ IU), vitamin E (425 IU), vitamin B12 (1,110 mcg), niacin (1,715 mg), pantothenic acid (8.5 mg), choline (425 mg), biotin (43 mcg), cobalt (1.7 mg), copper (8.5 mg), iron (17 mg), manganese (17 mg), zinc (43 mg) and trace quantities of riboflavin, thiamine, folic acid, vitamin K, vitamin C and selenium. The vitamin and mineral admixture is preferably combined with kelp, an acceptable and nutrient-rich feed grade carrier.

Capsule-in-a-capsule vehicles appropriate for administration to adult cattle contain live cell *Saccharomyces cerevisiae* yeast levels of $30\times10^9$ CFU per capsule.

The capsule-in-a-capsule vehicles are administered by standard Balling Gun techniques known in the veterinary and animal husbandry arts.

EXAMPLE 9

Preparation of Capsule-in-a-Capsule With the Probiotics Saccharomyces Cerevisiae (live cell culture) and Gastrointestinal Lactic Acid Producing Bacteria Capsule-in-a-capsule vehicles appropriate for administration to adult cattle are prepared by the method as described hereinbefore with the inner gelatin capsule containing the microorganisms. The microbial probiotic culture is a formulation of commercially available dormant live cell *Saccharomyces cerevisiae*, (ADY-20, available from Red Star Yeast Products, Milwaukee, Wis.) having a viability of $10\times10^9$ CFU/g and the lactic acid producing bacteria *Lactobacillus acidophilus*, *Lactobacillus lactis*, *Lactobacillus casei*, *Streptococcus faecium* and *Pediococcus cerevisiae*, (available from Agtech Products, Inc., Waukesha, Wis.; FarMor Biochem, Milwaukee, Wis.) having a viability of $20\times10^9$ CFU/g at the time of preparation.

The outer capsule contains the inner capsule and the vitamin and/or mineral admixture. Each capsule-in-a-capsule contains 5 g of *Saccharomyces cerevisiae* live cell culture and 0.25 g of lactic acid bacterial cultures (including standard formulation overages), and 6 g of vitamin and mineral admixture. The vitamin and mineral admixture is preferably combined with kelp, an acceptable and nutrient-rich feed grade carrier. The vitamins, minerals and kelp are in the outer capsule.

Capsule-in-a-capsule vehicles appropriate for administration to adult cattle contain live cell *Saccharomyces cerevisiae* yeast levels of $30\times10^9$ CFU per capsule, and lactic acid producing bacteria levels of $3\times10^9$ CFU per capsule. The vitamin and mineral admixture contains the following amounts per capsule as indicated in parentheses: vitamin A ($2.8\times10^5$ IU), vitamin $D_3$ ($4.2\times10^4$ IU), vitamin E (425 IU), vitamin B12 (1,110 mcg), niacin (1,715 mg), pantothenic acid (8.5 mg), choline (425 mg), biotin (43 mcg), cobalt (1.7 mg), copper (8.5 mg), iron (17 mg), manganese (17 mg), zinc (43 mg) and trace quantities of riboflavin, thiamine, folic acid, vitamin K, vitamin C and selenium.

The capsule-in-a-capsule vehicles are administered by standard Balling Gun techniques known in the veterinary and animal husbandry arts.

EXAMPLE 10

Preparation of Capsule-in-a-Capsule With the Probiotic *Bifidobacterium Longum*

Capsule-in-a-capsule vehicles appropriate for administration to adult cattle are prepared by the method as described hereinbefore with the inner gelatin capsule containing the microorganisms. The microorganisms are a formulation of commercially available dormant *Bifidobacterium longum*, (available from Agtech Products, Inc., Waukesha, Wis.; or Chr. Hansen's Laboratories, Milwaukee, Wis.) having a viability of $20\times10^9$ CFU/g at the time of preparation.

The outer capsule contains the inner capsule and the vitamin and/or mineral admixture. Each capsule-in-a-capsule contains 0.35 g of *Bifidobacterium longum* culture (including standard formulation overages), and 12.5 g of the vitamin and mineral admixture. The vitamin and mineral admixture is preferably combined with kelp, an acceptable and nutrient-rich feed grade carrier. The vitamins, minerals and kelp are in the outer capsule.

Capsule-in-a-capsule vehicles appropriate for administration to adult cattle contain bacterial levels of $4.5\times10^9$ CFU per capsule. The vitamin/mineral/kelp admixture contains the following amounts per capsule as indicated in parentheses: vitamin A ($5\times10^5$ IU), vitamin $D_3$ ($7.5\times10^4$ IU), vitamin E (750 IU), vitamin B12 (2,000 mcg), niacin (3,000 mg), pantothenic acid (15 mg), choline (750 mg), biotin (75 mcg), cobalt (3 mg), copper (15 mg), iron (30 mg), manganese (30 mg), zinc (75 mg) and trace quantities of riboflavin, thiamine, folic acid, vitamin K, vitamin C and selenium.

Capsule-in-a-capsule vehicles appropriate for administration to calves are prepared by an identical method, excepting that the vitamin and/or mineral admixture contains approximately one-third of the amounts of the vitamins and minerals enumerated above for use in the adult cattle capsule-in-a-capsules. The vitamin and mineral levels per capsule-in-a-capsule are as follows: vitamin A ($1.65\times10^5$ IU), vitamin $D_3$ ($2.5\times10^4$ IU), vitamin E (250 IU), vitamin B12 (650mcg), niacin (1,000 mg), pantothenic acid (5 mg), choline (250 mg), biotin (25 mcg), cobalt (1 mg), copper (5 mg), iron (10 mg), manganese (10 mg), zinc (25 mg) and trace quantities of riboflavin, thiamine, folic acid, vitamin K, vitamin C and selenium. Capsule-in-a-capsule vehicles appropriate for administration to calves contain bacterial levels of $4.5\times10^9$ CFU per capsule.

Each calf-size capsule-in-a-capsule contains approximately 0.35 g of bacterial culture (including standard formulation overages), and 3.5 g of the vitamin and mineral admixture. The vitamins and minerals are also preferably combined with kelp, an acceptable and nutrient-rich feed grade carrier.

EXAMPLE 11

Preparation of Capsule-in-a-Capsule With the Probiotic Bifidobacterium Longum and Gastrointestinal Lactic Acid Producing Bacteria Capsule-in-a-capsule vehicles appropriate for administration to adult cattle are prepared by the method as described hereinbefore with the inner gelatin capsule containing the microorganisms. The microorganisms are formulations of commercially available dormant cultures of the lactic acid producing bacteria *Lactobacillus acidophilus, Lactobacillus lactis, Lactobacillus casei, Streptococcus faecium* and *Pediococcus cerevisiae*, (available from Agtech Products, Inc., Waukesha, Wis.; FarMor Biochem, Milwaukee, Wis.) having a viability of $20 \times 10^9$ CFU/g and *Bifidobacterium longum*, (available from Agtech Products, Inc., Waukesha, Wis.; or Chr. Hansen's Laboratories, Milwaukee, Wis.) also having a viability of $20 \times 10^9$ CFU/g at the time of preparation.

The outer capsule contains the inner capsule and the vitamin and/or mineral admixture. Each capsule-in-a-capsule contains approximately 0.25 g of gastrointestinal lactic acid producing bacteria culture and approximately 0.13 g of *Bifidobacterium longum* culture, 0.38 g total (including standard formulation overages), and 12.5 g of the vitamin and mineral admixture. The vitamins and minerals preferably are combined with kelp, an acceptable and nutrient-rich feed grade carrier. The vitamins, minerals and kelp are in the outer capsule. Capsule-in-a-capsule vehicles appropriate for administration to adult cattle contain lactic acid producing bacterial levels of $3 \times 10^9$ CFU per capsule and *Bifidobacterium longum* bacterial levels of $1.7 \times 10^9$ CFU per capsule. The vitamin/mineral/kelp admixture contains the following amounts per capsule as indicated in parentheses: vitamin A ($5 \times 10^5$ IU), vitamin $D_3$ ($7.5 \times 10^4$ IU), vitamin E (750 IU), vitamin B12 (2,000 mcg), niacin (3,000 mg), pantothenic acid (15 mg), choline (750 mg), biotin (75 mcg), cobalt (3 mg), copper (15 mg), iron (30 mg), manganese (30 mg), zinc (75 mg) and trace quantities of riboflavin, thiamine, folic acid, vitamin K, vitamin C and selenium.

Capsule-in-a-capsule vehicles appropriate for administration to calves are prepared by an identical method, excepting that the vitamin and mineral admixture contains approximately one-third of the amounts of the vitamins and minerals enumerated above for use in the adult cattle capsule-in-a-capsules. The vitamin and mineral levels per capsule-in-a-capsule are as follows: vitamin A ($1.65 \times 10^5$ IU), vitamin $D_3$ ($2.5 \times 10^4$ IU), vitamin E (250 IU), vitamin B12 (650 mcg), niacin (1,000 mg), pantothenic acid (5 mg), choline (250 mg), biotin (25 mcg), cobalt (1 mg), copper (5 mg), iron (10 mg), manganese (10 mg), zinc (25 mg) and trace quantities of riboflavin, thiamine, folic acid, vitamin K, vitamin C and selenium. Capsule-in-a-capsule vehicles appropriate for administration to calves contain lactic acid producing bacterial levels of $3 \times 10^9$ CFU per capsule and *Bifidobacterium longum* bacterial levels of $1.7 \times 10^9$ CFU per capsule.

Each calf size capsule-in-a-capsule contains approximately 0.25 g of gastrointestinal lactic acid producing bacteria culture and approximately 0.13 g of *Bifidobacterium longum* culture, 0.38 g total (including standard formulation overages), and 3.5 g of the vitamin and mineral admixture. The vitamin and mineral admixture is also preferably combined with kelp, an acceptable and nutrient-rich feed grade carrier.

EXAMPLE 12

Preparation of Capsule-in-a-Capsule With the Probiotic *Propionibacterium freudenreicheii*

Capsule-in-a-capsule vehicles appropriate for administration to adult cattle are prepared by the method as described hereinbefore. The microbial culture is *Propionibacterium freudenreicheii* P5 strain having a viability of about $2 \times 10^{11}$ CFU/g at the time of preparation. The microbial culture is within the inner capsule.

The outer capsule contains the inner capsule and the vitamin and/or mineral admixture. Each capsule-in-a-capsule contains approximately 2 to 4 g of *Propionibacterium freudenreicheii* P5 strain culture (Bova-Pro, FarMor Biochem, Milwaukee, Wis.), including standard formulation overages, and approximately 9 g of the vitamin and mineral admixture. The vitamins and minerals are preferably combined with kelp, an acceptable and nutrient-rich feed grade carrier. The vitamins, minerals and kelp are in the outer capsule.

The vitamin and mineral levels per capsule-in-a-capsule are as follows: vitamin A ($4.25 \times 10^5$ IU), vitamin $D_3$ ($6.5 \times 10^4$ IU), vitamin E (645 IU), vitamin B12 (1,675 mcg), niacin (2,575 mg), pantothenic acid (12.9 mg), choline (645 mg), biotin (65 mcg), cobalt (2.6 mg), copper (12.9 mg), iron (25.7 mg), manganese (25.7 mg), zinc (64.3 mg) and trace quantities of riboflavin, thiamine, folic acid, vitamin K, vitamin C and selenium. Capsule-in-a-capsule vehicles appropriate for administration to adult cattle contain *Propionibacterium freudenreicheii* P5 strain bacterial levels of $2.5 \times 10^9$ to $5 \times 10^9$ CFU per capsule.

Propionibacterium species are rumen or gastrointestinal bacteria. Several species are approved for animal feeding. Various strains provide different metabolic activities. The P5 strain is a commercially available strain which utilizes rumen nitrate as a food substrate. In this invention, other strains are also used which have other beneficial activities such as utilizing lactic acid as a food substrate.

EXAMPLE 13

Preparation of Capsule-in-a-Capsule With Gastrointestinal Lactic Acid Producing Bacteria as the Probiotic Capsule-in-a-capsule vehicles appropriate for administration to adult cattle are prepared by the method as described hereinbefore. In this example, the vitamin and/or mineral admixture is contained in the inner capsule. The outer capsule contains the inner capsule and the probiotic gastrointestinal bacterial culture of the lactic acid producing bacteria *Lactobacillus acidophilus, Lactobacillus lactis, Lactobacillus casei, Streptococcus faecium* and *Pediococcus cerevisiae*. The probiotic gastrointestinal bacterial culture is a formulation of commercially available dormant *Lactobacillus acidophilus, Lactobacillus lactis, Lactobacillus casei, Streptococcus faecium* and *Pediococcus cerevisiae*, (available from Agtech Products, Inc., Waukesha, Wis.; FarMor Biochem, Milwaukee, Wis.) having a viability of $1.15 \times 10^9$ CFU/g at the time of preparation.

Each capsule-in-a-capsule contains 4 g of bacterial mixture (including standard formulation overages), and 6.3 g of vitamin and mineral admixture. The vitamins and minerals are preferably combined with kelp, an acceptable and nutrient-rich feed grade carrier.

Capsule-in-a-capsule vehicles appropriate for administration to adult cattle contain bacterial levels of $3 \times 10^9$ CFU per capsule. The vitamin and mineral admixture contains the following amounts per capsule as indicated in parentheses: vitamin A ($3 \times 10^5$ IU), vitamin $D_3$ ($4.5 \times 10^4$ IU), vitamin E (450 IU), vitamin B12 (1,170 mcg), niacin (1,800 mg), pantothenic acid (9 mg), choline (450 mg), biotin (45 mcg), cobalt (1.8 mg), copper (9 mg), iron (18 mg), manganese (18 mg), zinc (45 mg) and trace quantities of riboflavin, thiamine, folic acid, vitamin K, vitamin C and selenium.

Alternatively, the concentrations of respective vitamins and minerals in the admixture are modified to provide the equivalent absolute levels of vitamins and minerals listed in Example 7.

Capsule-in-a-capsule vehicles appropriate for administration to calves are prepared by an identical method, except that the vitamin and mineral admixture contains the identical levels per capsule-in-a-capsule of Example 7 as follows: vitamin A ($1.65 \times 10^5$ IU), vitamin $D_3$ ($2.5 \times 10^4$ IU), vitamin E (250 IU), vitamin B12 (650 mcg), niacin (1,000 mg), pantothenic acid (5 mg), choline (250 mg), biotin (25 mcg), cobalt (1 mg), copper (5 mg), iron (10 mg), manganese (10 mg), zinc (25 mg) and trace quantities of riboflavin, thiamine, folic acid, vitamin K, vitamin C and selenium. Capsule-in-a-capsule vehicles appropriate for administration to calves contain bacterial levels of $1.4 \times 10^9$ CFU per capsule.

Each calf-size capsule-in-a-capsule contains approximately 1.9 g of bacterial culture (including standard formulation overages), and 3.5 g of the vitamin and mineral admixture, the vitamins and minerals having also preferably been combined with kelp, an acceptable and nutrient-rich feed grade carrier.

Alternatively, the concentration of the bacterial culture is modified to provide the equivalent absolute levels of bacteria listed in Example 7.

EXAMPLE 14

Preparation of Capsule-in-a-Capsule With the Probiotic *Propionibacterium freudenreicheii*

Capsule-in-a-capsule vehicles appropriate for administration to adult cattle are prepared by the method as described hereinbefore. The inner capsule contains the vitamin and/or mineral admixture, and the outer capsule contains the inner capsule and probiotic microbial culture of *Propionibacterium freudenreicheii*.

The inner capsule's shell provides a barrier which prevents mixing of the probiotic culture (which is outside the shell of the inner capsule but within the outer capsule) with the vitamin and/or mineral admixture which is contained inside the inner capsule.

The microbial culture contains commercial formulations of *Propionibacterium freudenreicheii* having a viability of about $2 \times 10^{11}$ CFU/g at the time of preparation. Each capsule-in-a-capsule contains approximately 8 g of *Propionibacterium freudenreicheii* culture (Bova-Pro, FarMor Biochem, Milwaukee, Wis.), including standard formulation overages, and approximately 5 g of the vitamin and mineral admixture, the vitamins and minerals having preferably been combined with kelp, an acceptable and nutrient-rich feed grade carrier.

The vitamin and mineral levels per capsule-in-a-capsule are as follows: vitamin A ($2.35 \times 10^5$ IU), vitamin $D_3$ ($3.6 \times 10^4$ IU), vitamin E (360 IU), vitamin B12 (930 mcg), niacin (1,430 mg), pantothenic acid (7.1 mg), choline (360 mg), biotin (36 mcg), cobalt (1.4 mg), copper (7.1 mg), iron (14.3 mg), manganese (14.3 mg), zinc (36 mg) and trace quantities of riboflavin, thiamine, folic acid, vitamin K, vitamin C and selenium. Capsule-in-a-capsule vehicles appropriate for administration to adult cattle contain *Propionibacterium freudenreicheii* bacterial levels of $1 \times 10^{12}$ CFU per capsule.

The probiotic microorganisms described in this Example are primarily rumen organisms. The reversal in location of the microbial cultures and vitamin/trace mineral mixture is the most economically feasible process of accomplishing separation based on costs of different sizes of gelatin capsules and manufacturing equipment requirements and capabilities. This reverse compartmentalization also provides protection to the microbial cultures by the same physical separation of the cultures from the detrimental vitamin/trace mineral mixture as previously described. This preparation is especially designed for incoming feedlot cattle where body size requires lower nutritional levels and major dietary changes (forage ration switched to grain ration) and external stresses (e.g., shipping, grouping) produce primarily rumen acidosis. Microbial cultures chosen for this formulation are capable of reducing rumen lactic acidosis in these cattle. The mechanisms are *Propionibacterium freudenreicheii* producing propionate in the rumen, and enhancing the growth of other rumen or gastrointestinal bacteria which either utilize lactic acid in the rumen or ferment the common feedstuffs directly to absorbable volatile fatty acids (acetate, propionate, butyrate, etc.) to reduce acidity in the rumen (i.e., maintain a higher rumen pH).

EXAMPLE 15

Preparation of Capsule-in-a-Capsule With the Probiotic *Saccharomyces cerevisiae* (live cell)

Capsule-in-a-capsule vehicles appropriate for administration to adult cattle are prepared by the method as described hereinbefore. The inner capsule contains the vitamin and/or mineral admixture, and the outer capsule contains the inner capsule and probiotic microbial culture of live cell *Saccharomyces cerevisiae*.

The inner capsule's shell provides a barrier which prevents mixing of the probiotic culture (which is outside the shell of the inner capsule and within the outer capsule) with the vitamin and/or mineral admixture which is contained inside the inner capsule.

The microbial culture contains commercial formulations of live cell *Saccharomyces cerevisiae* having a viability of about $10 \times 10^9$ CFU/g at the time of preparation. The vitamin and/or mineral admixture is placed only within the inner capsule. Each capsule-in-a-capsule contains approximately 8 g of live cell *Saccharomyces cerevisiae* culture (ADY-20, Red Star Yeast Products, Milwaukee, Wis.), including standard formulation overages, and approximately 5 g of the vitamin and mineral admixture. The vitamin and mineral admixture is preferably combined with kelp, an acceptable and nutrient-rich feed grade carrier.

The vitamin and mineral levels per capsule-in-a-capsule are as follows: vitamin A ($2.35 \times 10^5$ IU), vitamin $D_3$ ($3.6 \times 10^4$ IU), vitamin E (360 IU), vitamin B12 (930 mcg), niacin (1,430 mg), pantothenic acid (7.1 mg), choline (360 mg), biotin (36 mcg), cobalt (1.4 mg), copper (7.1 mg), iron (14.3 mg), manganese (14.3 mg), zinc (36 mg) and trace quantities of riboflavin, thiamine, folic acid, vitamin K, vitamin C and selenium. Capsule-in-a-capsule vehicles appropriate for administration to adult cattle contain live cell *Saccharomyces cerevisiae* yeast levels of $50 \times 10^9$ CFU per capsule.

The reversal in location of the microbial cultures and vitamin/trace mineral mixture is the most economically feasible process of accomplishing separation based on costs of different sizes of gelatin capsules and manufacturing equipment requirements and capabilities. This reverse compartmentalization also provides protection to the microbial cultures by the same physical separation of the cultures from the detrimental vitamin/trace mineral mixture as previously described. This preparation is especially designed for incoming feedlot cattle where body size requires lower nutritional levels and major dietary changes (forage ration switched to grain ration) and external stresses (e.g., shipping, grouping) produce primarily rumen acidosis.

EXAMPLE 16

Preparation of Capsule-in-a-Capsule With the Probiotics *Propionibacterium freudenreicheii*, *Saccharomyces cerevisiae* (live cell), and *Aspergillus oryzae*

Capsule-in-a-capsule vehicles appropriate for administration to adult cattle are prepared by the method as described hereinbefore. The inner capsule contains the vitamin and/or mineral admixture, and the outer capsule contains the inner capsule and probiotic microbial culture of *Propionibacterium freudenreicheii*, live cell *Saccharomyces cerevisiae*, and *Aspergillus oryzae*.

The inner capsule shell provides a barrier which prevents mixing of the probiotic culture (which is outside the shell of the inner capsule and within the outer capsule) with the vitamin and/or mineral admixture which is contained inside the inner capsule.

The microbial culture contains formulations of commercially available *Propionibacterium freudenreicheii*, live cell *Saccharomyces cerevisiae*, and *Aspergillus oryzae* having viabilities of about $2\times10^{11}$ CFU/g, $10\times10^9$ CFU/g and $1\times10^7$ CFU/g, respectively, at the time of preparation. The vitamin and mineral admixture is placed only within the inner capsule. Each capsule-in-a-capsule contains approximately 2 g of *Propionibacterium freudenreicheii* culture (Bova-Pro, FarMor Biochem, Milwaukee, Wis.), 5 g of live cell *Saccharomyces cerevisiae* culture (ADY-20, Red Star Yeast Products, Milwaukee, Wis.), and 2 g of Aspergillus oryzae culture (Agtech Products, Inc., Waukesha, Wis.), including standard formulation overages, and approximately 5 g of the vitamin and mineral admixture. The vitamin and mineral admixture is preferably combined with kelp, an acceptable and nutrient-rich feed grade carrier.

The vitamin and mineral levels per capsule-in-a-capsule are as follows: vitamin A ($2.35\times10^5$ IU), vitamin $D_3$ ($3.6\times10^4$ IU), vitamin E (360 IU), vitamin B12 (930 mcg), niacin (1,430 mg), pantothenic acid (7.1 mg), choline (360 mg), biotin (36 mcg), cobalt (1.4 mg), copper (7.1 mg), iron (14.3 mg), manganese (14.3 mg), zinc (36 mg) and trace quantities of riboflavin, thiamine, folic acid, vitamin K, vitamin C and selenium. Capsule-in-a-capsule vehicles appropriate for administration to adult cattle contain *Propionibacterium freudenreicheii* bacterial levels of $2.5\times10^{11}$ CFU per capsule, live cell *Saccharomyces cerevisiae* yeast levels of $30\times10^9$ CFU per capsule, and *Aspergillus oryzae* fungal levels of $2\times10^7$ CFU per capsule.

The probiotic microorganisms described in this section are primarily rumen organisms. The reversal in location of the microbial cultures and vitamin/trace mineral mixture is the most economically feasible process of accomplishing separation based on costs of different sizes of gelatin capsules and manufacturing equipment requirements and capabilities. This reverse compartmentalization also provides protection to the microbial cultures by the same physical separation of the cultures from the detrimental vitamin/trace mineral mixture as previously described. This preparation is especially designed for incoming feedlot cattle where body size requires lower nutritional levels and major dietary changes (forage ration switched to grain ration) and external stresses (e.g., shipping, grouping) produce primarily rumen acidosis. Microbial cultures chosen for this formulation are capable of reducing rumen lactic acidosis in these cattle. The mechanisms are *Propionibacterium freudenreicheii* producing propionate in the rumen, and live cell yeast and fungal cultures enhancing the growth of other rumen or gastrointestinal bacteria which either utilize lactic acid in the rumen or ferment the common feedstuffs directly to absorbable volatile fatty acids (acetate, propionate, butyrate, etc.) to reduce acidity in the rumen (i.e., maintain a higher rumen pH).

EXAMPLE 17

Preparation of Capsule-in-a-Capsule With the Probiotics *Propionibacterium freudenreicheii*, *Saccharomyces cerevisiae*(live cell), and *Aspergillus oryzae* and Gastrointestinal Lactic Acid Producing Bacteria Capsule-in-a-capsule vehicles appropriate for administration to adult cattle are prepared by the method as described hereinbefore. In this embodiment, as in Example 16, the vitamin and/or mineral admixture is in the inner capsule. In this Example, the outer capsule contains the inner capsule and probiotic microbial culture of *Propionibacterium freudenreicheii*, live cell *Saccharomyces cerevisiae*, and *Aspergillus oryzae*, and *Lactobacillus acidophilus*, *Lactobacillus lactis*, *Lactobacillus casei*, *Streptococcus faecium* and *Pediococcus cerevisiae*.

The gastrointestinal lactic acid producing bacterial cultures are formulations of commercially available dormant *Lactobacillus acidophilus*, *Lactobacillus lactis*, *Lactobacillus casei*, *Streptococcus faecium* and *Pediococcus cerevisiae* having a viability of $20\times10^9$ CFU/g at time of preparation (available from Agtech Products, Inc., Waukesha, Wis. and FarMor Biochem, Milwaukee, Wis.) and commercial formulations of *Propionibacterium freudenreicheii*, live cell *Saccharomyces cerevisiae*, and *Aspergillus oryzae* having viabilities of about $2\times10^{11}$ CFU/g, $10\times10^9$ CFU/g and $1\times10^7$ CFU/g, respectively, at the time of preparation. The vitamin and/or mineral admixture is placed only within the inner capsule. Each capsule-in-a-capsule contains approximately 2 g of *Propionibacterium freudenreicheii* culture (Bova-Pro, FarMor Biochem, Milwaukee, Wis.), 5 g of live cell *Saccharomyces cerevisiae* culture (ADY-20, Red Star Yeast Products, Milwaukee, Wis.), and 2 g of *Aspergillus oryzae* culture (Agtech Products, Inc., Waukesha, Wis.), and 0.25 g of the lactic acid producing bacteria culture, including standard formulation overages, and approximately 5 g of the vitamin and mineral admixture. The vitamin and mineral admixture is preferably combined with kelp, an acceptable and nutrient-rich feed grade carrier.

The vitamin and mineral levels per capsule-in-a-capsule are as follows: vitamin A ($2.35\times10^5$ IU), vitamin $D_3$ ($3.6\times10^4$ IU), vitamin E (360 IU), vitamin B12 (930 mcg), niacin (1,430 mg), pantothenic acid (7.1 mg), choline (360 mg), biotin (36 mcg), cobalt (1.4 mg), copper (7.1 mg), iron ( 14.3 mg), manganese (14.3 mg), zinc (36 mg) and trace quantities of riboflavin, thiamine, folic acid, vitamin K, vitamin C and selenium. Capsule-in-a-capsule vehicles appropriate for administration to adult cattle contain *Propionibacterium freudenreicheii* bacterial levels of $2.5\times10^{11}$ CFU per capsule, live cell *Saccharomyces cerevisiae* yeast levels of $30 \times 10^9$ CFU per capsule, *Aspergillus oryzae* fungal levels of $2 \times 10^7$ CFU per capsule, and lactic acid producing bacteria levels of $3 \times 10^9$ CFU per capsule.

EXAMPLE 18

Preparation of Capsule-in-a-Capsule With the Probiotics Propionibacterium species, *Saccharomyces cerevisiae* (live cell), and *Aspergillus oryzae*

Capsule-in-a-capsule vehicles appropriate for administration to incoming feedlot cattle and adult cattle suffering from rumen acidosis are prepared by the method as described hereinbefore. In this embodiment, the vitamin and/or mineral admixture is contained in the inner capsule. The outer capsule contains the inner capsule and probiotic microbial culture of Propionibacterium species, live cell *Saccharomyces cerevisiae*, and *Aspergillus oryzae*.

The microbial culture contains formulations of commercially available cultures of Propionibacterium species, live cell *Saccharomyces cerevisiae*, and *Aspergillus oryzae* having viabilities of about $2 \times 10^{11}$ CFU/g, $10 \times 10^9$ CFU/g and $1 \times 10^7$ CFU/g, respectively, at the time of preparation. The vitamin and/or mineral admixture is placed only within the inner capsule. Each capsule-in-a-capsule contains approximately 9 g of microbial cultures consisting of approximately 5 g of Propionibacterium species culture (Bova-Pro, FarMor Biochem, Milwaukee, Wis.), 2 g of live cell *Saccharomyces cerevisiae* culture (ADY-20, Red Star Yeast Products, Milwaukee, Wis.), and 2 g. of *Aspergillus oryzae* culture (Agtech Products, Inc., Waukesha, Wis.), including standard formulation overages, and approximately 5 g of the vitamin and mineral admixture. The vitamin and mineral admixture is preferably combined with kelp, an acceptable and nutrient-rich feed grade carrier.

The vitamin and mineral levels per capsule-in-a-capsule are as follows: vitamin A ($2.35 \times 10^5$ IU), vitamin $D_3$ ($3.6 \times 10^4$ IU), vitamin E (360 IU), vitamin B12 (930 mcg), niacin (1,430 mg), pantothenic acid (7.1 mg), choline (360 mg), biotin (36 mcg), cobalt (1.4 mg), copper (7.1 mg), iron (14.3 mg), manganese (14.3 mg), zinc (36 mg) and trace quantities of riboflavin, thiamine, folic acid, vitamin K, vitamin C and selenium. Capsule-in-a-capsule vehicles appropriate for administration to adult cattle contain Propionibacterium bacterial levels of $6.5 \times 10^{11}$ CFU per capsule, live cell *Saccharomyces cerevisiae* yeast levels of $13 \times 10^9$ CFU per capsule, and *Aspergillus oryzae* fungal levels of $2 \times 10^7$ CFU per capsule.

One to two capsule-in-a-capsule vehicles are administered daily for 1 to 3 days to incoming feedlot cattle and to dairy cows suffering from rumen acidosis. The administration is done using a standard balling gun technique.

EXAMPLE 19

Preparation of Capsule-in-a-Capsule With the Probiotic *Propionibacterium freudenreicheii*

Capsule-in-a-capsule vehicles appropriate for administration to adult cattle for nitrate toxicity are prepared by the method as described hereinbefore. The microbial culture is *Propionibacterium freudenreicheii* P5 strain having a viability of about $2 \times 10^{11}$ CFU/g at time of preparation. The vitamin and/or mineral admixture is vitamin A ($1 \times 10^6$ IU). Approximately 1.7 g vitamin A supplement is in the inner capsule. The outer capsule contains the inner capsule and the probiotic microbial culture *Propionibacterium freudenreicheii*. Each capsule-in-a-capsule contains approximately 9 g of *Propionibacterium freudenreicheii* P5 strain culture (Bova-Pro, FarMor Biochem, Milwaukee, Wis.), including standard formulation overages, (approximately $1.2 \times 10^{12}$ CFU/capsule) at time of preparation.

One capsule-in-a-capsule vehicle is administered daily for 1 to 3 days to cattle prior to exposing the cattle to high nitrate feeds. Alternatively, one capsule-in-a-capsule vehicle is administered daily for 3 to 7 days in conjunction with veterinary therapy for acute nitrate toxicity in cattle.

EXAMPLE 20

Preparation of Capsule-in-a-Capsule With the Probiotic *Propionibacterium freudenreicheii*

Capsule-in-a-capsule vehicles appropriate for administration to adult cattle for nitrate toxicity are prepared by the method as described hereinbefore. The microbial culture is *Propionibacterium freudenreicheii* P5 strain having a viability of $2 \times 10^{11}$ CFU/g ($5.3 \times 10^{11}$ CFU per capsule), at time of preparation. The microbial culture is in the inner capsule. The outer capsule contains the inner capsule and the vitamin and/or mineral admixture. The vitamin and/or mineral admixture is vitamin A ($1 \times 10^6$ IU). Humic acid (dried humates available as AgroLig, American Colloid Co., Arlington Heights, Ill.) is admixed with the vitamin A. Humates are organic acids which are obtained from humus. The vitamin A/humic acid admixture is contained in the outer capsule. Each capsule-in-a-capsule contains approximately 9.5 g of vitamin A/humic acid admixture (1.7 g vitamin A supplement, 7.8 g dried humates) and approximately 4 g of *Propionibacterium freudenreicheii* P5 strain culture (Bova-Pro, FarMor Biochem, Milwaukee, Wis.), including standard formulation overages.

The uses and suggested administration is the same as given in Example 19.

EXAMPLE 21

Preparation of Capsule-in-a-Capsule With the Probiotic Gastrointestinal Lactic Acid Producing Bacteria *Lactobacillus acidophilus*, *Lactobacillus casei*, and *Streptococcus faecium* for Administration to Ratites Such as Ostriches or Emus Capsule-in-a-capsule vehicles appropriate for administration to ostriches or emus are prepared by the method as described hereinbefore. In this embodiment, the outer capsule contains the vitamin and/or mineral admixture and the inner capsule. The inner capsule contains the gastrointestinal lactic acid producing bacterial cultures of *Lactobacillus acidophilus*, *Lactobacillus casei*, and *Streptococcus faecium*.

The microbial culture is a formulation of dormant commercially available cultures of the lactic acid producing bacteria *Lactobacillus acidophilus*, *Lactobacillus casei*, and *Streptococcus faecium*, (available from Agtech Products, Inc., Waukesha, Wis.; FarMor Biochem, Milwaukee, Wis.) having a viability of $20 \times 10^9$ CFU/g at the time of preparation.

Each capsule-in-a-capsule contains approximately 0.25 g of bacterial culture (including standard formulation overages), and 1.8 g of the vitamin and mineral admixture. The vitamin and mineral admixture is preferably combined with kelp, an acceptable and nutrient-rich feed grade carrier.

Each capsule-in-a-capsule vehicle contains bacterial levels of $3\times10^9$ CFU per capsule. The vitamin/mineral/kelp admixture contains the following amounts per capsule as indicated in parentheses: vitamin A ($8.5\times10^4$ IU), vitamin $D_3$ ($1.3\times10^4$ IU), vitamin E (130 IU), vitamin B12 (335 mcg), niacin (515 mg), pantothenic acid (2.6 mg), choline (130 mg), biotin (13 mcg), cobalt (0.5 mg), copper (2.6 mg), iron (5.1 mg), manganese (5.1 mg), zinc (12.9 mg) and trace quantities of riboflavin, thiamine, folic acid, vitamin K, vitamin C and selenium.

The preparation is especially designed for ratites during periods of stress, in conjunction with veterinary therapy, antibiotics or surgery. The preparation can be used on adult and juvenile ratites being fed alfalfa and forage based rations.

EXAMPLE 22

Preparation of Capsule-in-a-Capsule With the Probiotic Gastrointestinal Lactic Acid Producing Bacteria *Lactobacillus acidophilus, Lactobacillus casei*, and *Streptococcus faecium* for Administration to Ratites Such as Ostriches or Emus Capsule-in-a-capsule vehicles appropriate for administration to ostriches or emus are prepared by the method as described hereinbefore. In this embodiment, the outer capsule contains the inner capsule and the vitamin and/or mineral admixture. The inner capsule contains the gastrointestinal lactic acid producing bacterial cultures of *Lactobacillus acidophilus, Lactobacillus casei*, and *Streptococcus faecium*.

The microbial culture is a formulation of dormant commercially available cultures of the lactic acid producing bacteria *Lactobacillus acidophilus, Lactobacillus casei*, and *Streptococcus faecium*, (available from Agtech Products, Inc., Waukesha, Wis.; FarMor Biochem, Milwaukee, Wis.) having a viability of $20\times10^9$ CFU/g at the time of preparation.

Each capsule-in-a-capsule contains approximately 0.25 g of bacterial culture (including standard formulation overages), and 5 g of the vitamin and mineral admixture.

Each capsule-in-a-capsule vehicle contains bacterial levels of $3\times10^9$ CFU per capsule. The vitamin and mineral admixture contains the following amounts per capsule as indicated in parentheses: vitamin A ($2.35\times10^5$ IU), vitamin $D_3$ ($3.6\times10^4$ IU), vitamin E (360 IU), vitamin B12 (930 mcg), niacin (1,430 mg), pantothenic acid (7.1 mg), choline (360 mg), biotin (36 mcg), cobalt (1.4 mg), copper (7.1 mg), iron (14.3 mg), manganese (14.3 mg), zinc (36 mg) and trace quantities of riboflavin, thiamine, folic acid, vitamin K, vitamin C and selenium. The vitamin and mineral admixture is preferably combined with kelp, an acceptable and nutrient-rich feed grade carrier.

The preparation is especially designed for ratites during periods of stress, in conjunction with veterinary therapy, antibiotics or surgery. The preparation is most useful where the ratite is an adult or is being fed corn or grain based rations.

EXAMPLE 23

Preparation of Capsule-in-a-Capsule With the Probiotic *Aspergillus oryzae*

Capsule-in-a-capsule vehicles appropriate for administration to adult cattle are prepared by the method as described hereinbefore. The microbial culture is *Aspergillus oryzae* having a viability of about $1\times10^7$ CFU/g at the time of preparation. The microbial culture is within the inner capsule.

The outer capsule contains the inner capsule and the vitamin and/or mineral admixture. Each capsule-in-a-capsule contains approximately 2 to 4 g of *Aspergillus oryzae* culture (Agtech Products, Inc., Waukesha, Wis.), including standard formulation overages, and approximately 9 g of the vitamin and mineral admixture. The vitamins and minerals are preferably combined with kelp, an acceptable and nutrient-rich feed grade carrier. The vitamins, minerals and kelp are in the outer capsule.

The vitamin and mineral levels per capsule-in-a-capsule are as follows: vitamin A ($4.25\times10^5$ IU), vitamin $D_3$ ($6.5\times10^4$ IU), vitamin E (645 IU), vitamin B12 (1,675 mcg), niacin (2,575 mg), pantothenic acid (12.9 mg), choline (645 mg), biotin (65 mcg), cobalt (2.6 mg), copper (12.9 mg), iron (25.7 mg), manganese (25.7 mg), zinc (64.3 mg) and trace quantities of riboflavin, thiamine, folic acid, vitamin K, vitamin C and selenium. Capsule-in-a-capsule vehicles appropriate for administration to adult cattle contain *Aspergillus oryzae* levels of $2\times10^7$ to $4\times10^7$ CFU per capsule.

EXAMPLE 24

Preparation of Capsule-in-a-Capsule with the Probiotics Selected from the List of Direct-Fed Microorganisms Reviewed by the Food and Drug Administration, Center for Veterinary Medicine. (Direct-fed Microbials in the Inner Capsule)

Capsule-in-a-capsule vehicles appropriate for administration to livestock or ratites are prepared by the method described hereinbefore. In this Example, the probiotic is in the inner capsule, and the outer capsule contains the inner capsule and the vitamin and/or mineral admixture. The vitamin and/or mineral admixture is formulated to the specific animal, its age and for the specific dietary purpose. The probiotic is selected from the list of non-spore forms and/or live cell culture forms of Direct-Fed Microorganisms reviewed by the Food and Drug Administration Center for Veterinary Medicine. By nonspore forms is meant that the probiotic culture does not exist solely in the spore form. Where yeast is selected as a probiotic, only a live cell yeast culture is used. The probiotic culture is present in a quantity at least sufficient to produce the sought after biological effect. The vitamins and/or mineral admixture is preferably combined with kelp, an acceptable and nutrient-rich feed grade carrier.

EXAMPLE 25

Preparation of Capsule-in-a-Capsule with Probiotics Selected from the List of Direct-Fed Microorganisms Reviewed by the Food and Drug Administration, Center for Veterinary Medicine. (Vitamin and/or Mineral Admixture in the Inner Capsule)

Capsule-in-a-capsule vehicles appropriate for administration to livestock or ratites are prepared by the method described hereinbefore. In this Example, the vitamin and/or mineral admixture is in the inner capsule; and the outer capsule contains the inner capsule and the probiotic. The vitamin and/or mineral admixture is formulated to the specific animal, its age and for the specific dietary purpose. The probiotic is selected from the list of non-spore forms and/or live cell culture forms of Direct-Fed Microorganisms reviewed by the Food and Drug Administration Center for Veterinary Medicine as in Example 24. By non-spore forms is meant that the probiotic culture does not exist solely in the spore form. Where yeast is selected as a probiotic, only a live cell yeast culture is used. The probiotic culture is present in a quantity at least sufficient to produce the sought after biological effect. The vitamins and/or mineral admixture is preferably combined with kelp, an acceptable and nutrient-rich feed grade carrier.

EXAMPLE 26

Decrease of Viability of Probiotic *Propionibacterium freudenreichii* Colony Forming Units Where Probiotic is Mixed with Vitamin and/or Mineral Admixtures and Other Feeding Substances

*Propionibacterium freudenreichii* P5 strain culture (Bova-Pro™, Far-Mor Biochem, Milwaukee, Wis.) was variously tested against a vitamin/mineral/kelp formulation appropriate for administration to adult cattle as described in Example 7, dried humates (humic acid, typical pH about 4.0), a culture containing yeast metabolites and growth media, montmorillonite clay, and a proprietary sulfated trace mineral mixture. Humic acid and montmorillonite clay absorb nitrates on their surface.

The samples included single capsule forms enclosing the culture and various vitamin and mineral admixtures or other feeding substances.

Six sample formulations were prepared as follows: Sample P1 was the control culture of *Propionibacterium freudenreichii* P5 strain, (Bova-Pro™, Far-Mor Biochem, Milwaukee, Wis.). Sample P2 was a mixture of 10% P1 culture and 90% of the vitamin/mineral/kelp admixture as described in Example 7 (for adult cattle). Sample P3 was a mixture of 10% P1 culture and 90% dried humates. Sample P4 was a mixture of 10% P1 culture and 90% culture containing yeast, yeast metabolites and yeast growth media (*Saccharomyces cerevisiae* yeast culture, Diamond V Mills, Cedar Rapids, Iowa. This culture is not considered a live cell yeast culture for purposes of this invention.) Sample P5 was a mixture of 10% P1 culture and 90% montmorillonite clay (trade name Dynamin). Sample P6 was a mixture of 10% P1 culture and 90% proprietary sulfated trace mineral mixture (trade name Midwestern Bio-Ag's TM Mix, available from Midwestern Bio-Ag Products & Services, Inc., Blue Mounds, Wis.). The percentages are percentages by weight.

Samples were assembled and counts were conducted by a microbiological laboratory on Day 0 and Day 30. Microorganisms were enumerated and counted using an AFIA accepted protocol performed by Agtech Products, Inc., Waukesha, Wis., for dilution, plating and counting of the microorganisms, Each test sample was individually serially diluted with a sterile 0.1% peptone solution. Appropriate sized aliquots of each diluted test sample were transferred into separate sterile petri dishes. Ten to twelve ml of sterilized Sodium Lactate Agar(NLA) was added to each petri dish with swirling. Sodium Lactate Agar is a general agar for the enumeration of Propionibacteria from dairy or other food products. The plates were covered and cooled to room temperature before being inverted and placed into GasPak™ anaerobic jars. The plates were incubated at 30°–32° C. for seven days. Visible colonies take approximately five to seven days to form. Colonies were then counted using a Quebec colony counter. Counting results were reported on a CFU/g basis. Initial microbial counts and the Percent Microbial Survival after 30 days are given in Table 5 below.

TABLE 5

| | Propionibacteria counts (CFU/gram) | | |
|---|---|---|---|
| | Time (days) | | Percent Microbial |
| Treatment | 0 | 30 | Survival |
| P1 | 1.5E+11 | 6.1E+10 | $4.1 \times 10^1\%$ |
| P2 | 2.10E+10 | 6.90E+08 | $3.3 \times 10^0\%$ |
| P3 | 2.40E+10 | 1.00E+04 | $4.0 \times 10^{-5}\%$ |
| P4 | 2.30E+10 | 2.80E+07 | $1.2 \times 10^{-1}\%$ |
| P5 | 4.40E+10 | 5.40E+07 | $1.2 \times 10^{-1}\%$ |
| P6 | $2.60E+08^A$ | 8.70E+05 | $3.3 \times 10^{-1}\%$ |

Percent Microbial Survival = $\frac{\text{Day 30 count}}{\text{Day 0 count}} \times 100\%$ $^A$Varied significantly from theoretical starting count of 2.00E+10 CFU/gram. Approximate theoretical starting counts: P1 = 2.0E+11 CFU/gram; P2, P3, P4, P5, P6 = 2.0E+10 CFU/gram.

Percent microbial survival of the Propionibacteria at 30 days was significantly lower for all samples as compared to the control sample. Sample P2 percent survival was $3.3\times 10^0\%$ versus $4.1\times 10^1\%$ for the control. Level of significance was determined as greater than one log 10 of magnitude difference between Percent Microbial Survival for the samples as compared to the Percent Microbial Survival of the control sample.

EXAMPLE 27

Comparative Effectiveness of Capsule-in-a-Capsule Packaging System and Single Capsule Preparation in terms of Decrease of Viability of Microbials Over Time Capsule-in-a-capsule vehicles appropriate for administration to adult cattle are prepared and tested against single capsule preparations having an admixture of microorganism cultures and nutrient supplements identical in concentrations (i.e., in percent by weight) to the respective capsule-in-a-capsule vehicles. Control samples consist of cultures only (i.e., 100% by weight) enclosed in a gelatin capsule. All capsules and capsule-in-a-capsule vehicles are stored at room temperature following preparation.

Thirteen samples including controls are prepared as follows:

Samples containing Bifidobacterium species:

Sample B1 is prepared using the capsule-in-a-capsule vehicle as disclosed in Example 10, with the inner capsule containing approximately 0.35 grams *Bifidobacterium longum* culture, guaranteed at $20\times 10^9$ CFU/gram (2.7% by weight of net contents), and the outer capsule containing approximately 12.5 grams of the vitamin/mineral/kelp mixture (97.3% by weight of net contents). Counts are conducted on inner capsule contents.

Sample B2 is prepared using a mixture of 2.7% by weight of *Bifidobacterium longum* culture (guaranteed at $20\times 10^9$ CFU/gram) and 97.3% by weight of the vitamin/mineral/kelp mixture as disclosed in Example 10. The culture and the vitamin/mineral/kelp admixture are admixed and packaged into a single gelatin capsule. The count is conducted on the entire capsule contents.

Sample B3 is the control sample. It is prepared by packaging only Bifidobacterium longum culture (guaranteed at 20×10$^9$ CFU/gram) into a gelatin capsule (100% by weight).

Samples containing Propionibacterium species:

sample P1 is prepared as disclosed in Example 12, using the capsule-in-a-capsule vehicle with the inner capsule containing approximately 4 grams *Propionibacterium freudenreichii* culture, guaranteed at 2×10$^{11}$ CFU/gram, (30.8% by weight of net contents), and the outer capsule containing approximately 9 grams of the vitamin/mineral/kelp mixture (69.2% by weight of net contents). Counts are conducted on the inner capsule contents.

Sample P2 is prepared using a mixture of 30.8% by weight of *Propionibacterium freudenreichii* culture (guaranteed at 2×10$^{11}$ CFU/gram) and 69.2% of the vitamin/mineral/kelp mixture (the admixture as described in Example 12), by weight, packaged into a single gelatin capsule. The counts are conducted on the entire capsule contents.

Sample P3 is prepared as disclosed in Example 14, using the capsule-in-a-capsule vehicle with the inner capsule containing approximately 5 grams of the vitamin/mineral/kelp mixture (38.5% by weight of net contents), and the outer capsule containing approximately 8 grams *Propionibacterium freudenreichii* culture, guaranteed at 2×10$^{11}$ CFU/gram, (61.5% by weight of net contents). Counts are conducted on the outer capsule probiotic contents.

Sample P4 is prepared as disclosed in Example 20, using the capsule-in-a-capsule vehicle with the inner capsule containing approximately 4 grams *Propionibacterium freudenreichii* culture, guaranteed at 2×10$^{11}$ CFU/gram (29.6% by weight of net contents), and the outer capsule containing approximately 9.5 grams of the vitamin A and humic acid mixture (70.4% by weight of net contents). Counts are conducted on the inner capsule contents.

Sample P5 is prepared using a mixture of 29.6% *Propionibacterium freudenreichii* culture (guaranteed at 2×10$^{11}$ CFU/gram) and 70.4% the vitamin A and humic acid mixture (the same admixture as disclosed in Example 20), by weight, and packaged into a single gelatin capsule. Counts are conducted on entire capsule contents.

Sample P6 is a control sample. It is prepared by packaging only *Propionibacterium freudenreichii* culture (guaranteed at 2×10$^{11}$ CFU/gram) into a gelatin capsule (100% by weight).

Samples containing *Saccharomyces cerevisiae*(live cell yeast):

Sample Y1 is prepared as disclosed in Example 8, using the capsule-in-a-capsule vehicle with the inner capsule containing approximately 5 grams of live cell *Saccharomyces cerevisiae* culture, guaranteed at 10×10$^9$ CFU/gram, (45.5% by weight of net contents), and the outer capsule containing approximately 6 grams of the vitamin/mineral/kelp admixture (54.5% by weight of net contents. Counts are conducted on the inner capsule contents.

Sample Y2 is prepared using a mixture of 45.5% live cell *Saccharomyces cerevisiae* culture (guaranteed at 10×10$^9$ CFU/gram) and 54.5% of the vitamin/mineral/kelp admixture (as disclosed in Example 8), by weight, packaged into a single gelatin capsule. Counts are conducted on the entire capsule contents.

Sample Y3 is prepared as is disclosed in example 15, using the capsule-in-a-capsule vehicle, with inner capsule containing approximately 5 grams of the vitamin/mineral/kelp admixture (38.5% by weight of net contents), and outer capsule containing approximately 8 grams live cell *Saccharomyces cerevisiae* culture, guaranteed at 10×10$^9$ CFU/gram, (61.5% by weight of net contents). Counts are conducted on the outer capsule probiotic contents.

Sample Y6 is the control sample. It is prepared by packaging only live cell *Saccharomyces cerevisiae* culture (guaranteed at 10×10$^9$ CFU/gram) into a gelatin capsule (100% by weight).

The samples are assembled and the counts are conducted by a microbiological laboratory on Day 0, Day 30, and Day 60 or later. The microorganisms are enumerated and counted using industry accepted protocols, such as the American Feed Ingredient Association(AFIA) accepted protocols for dilution, plating and counting of the respective culture types. Likewise, accepted growth media agar specific for the respective culture (Bifidobacteria, Propionibacteria, and Saccharomyces) is used. Results are reported and percent microbial survival versus time for each of the various samples is compared with the respective control sample's percent microbial survival versus time.

More specifically, according to the appropriate protocol, one or 11 gram samples of microorganisms, depending on texture and uniformity, are serially diluted, plated with the appropriate growth medium agar onto sterile Petri plates, and incubated until colonies are readily discernible and identifiable. Colonies are counted using a Quebec colony counter on days 0, 30 and day 60 or later, i.e., for example day 64. Counting results are reported on a CFU/g basis. Initial microbial counts and percent microbial survival over time are calculated for the various samples and controls. The results show a higher percent microbial survival over time for the capsule-in-a-capsule samples as compared to the single capsule formulations, where the single formulation is the admixture of the microbial with the nutritional supplement.

While the present invention has now been described and exemplified with some specificity, those skilled in the art will appreciate the various modifications, including variations, additions and omissions, that may be made in what has been described. Accordingly, it is intended that these modifications also be encompassed by the present invention and that the scope of the present invention be limited solely by the broadest interpretation that lawfully can be accorded the appended claims.

I claim:

1. A dietary adjunct composition comprising:
   a double capsule, said double capsule including an inner capsule and an outer capsule spaced apart and enclosing said inner capsule,
   a) said inner capsule including a dissolvable gelatin shell and a first substance therein,
   b) said outer capsule including a dissolvable gelatin shell and a second substance therein; wherein, one of said substances is viable gastrointestinal microorganisms and the other said substance is a nutritional supplement having the property of diminishing viability of said microorganisms; wherein said microorganisms are selected from the group consisting of gastrointestinal bacteria, live cell yeasts, fungi and a combination thereof; wherein said bacteria are one or more of the genus Lactobacillus, Streptococcus, Pediococcus, Bifidobacterium, or Propionibacterium; wherein said live cell yeast is the genus Saccharomyces; wherein said fungus is the genus Aspergillus; and wherein said nutritional supplement is selected from the group consisting of vitamins, minerals, and a combination thereof; said vitamins including one or more of vitamin A, vitamin D, vitamin E, vitamin $B_{12}$, riboflavin, niacin, pantothenic acid, thiamine, choline, folic acid, biotin, vitamin K, and vitamin C; and said minerals including one or more of cobalt, copper, iron, manganese, zinc, and selenium.

2. The composition of claim 1, wherein said first substance is said microorganisms and said second substance is said nutritional supplement.

3. The composition of claim 1, wherein said first substance is said nutritional supplement and said second substance is said microorganisms.

4. The composition of claim 1 wherein said microorganisms are live cell cultures of *Sacchromyces cerevisiae*.

5. The composition of claim 1 wherein said microorganisms are *Aspergillus oryzae*.

6. The composition of claim 1 wherein said nutritional supplement is admixed with an acceptable feed grade carrier.

7. A dietary adjunct composition comprising:
   a) a double capsule, said double capsule including an inner capsule and an outer capsule spaced apart and enclosing said inner capsule, said inner capsule including a dissolvable gelatin shell, said outer capsule including a dissolvable gelatin shell,
   b) viable microorganisms within said double capsule, wherein said microorganisms are bacteria, fungi or live cell cultures of yeast or a combination thereof, wherein said bacteria include one or more of the genus Lactobacillus, Streptococcus, Pediococcus, Bifidobacterium, or Propionibacterium; wherein said fungi is the genus Aspergillus; and wherein said yeast is the species *Saccharomyces cerevisiae*; and
   c) a nutritional supplement within said double capsule, said nutritional supplement separated from said microorganisms by said gelatin shell of said inner capsule, wherein said nutritional supplement is selected from the group consisting of vitamins, minerals, and a combination of thereof, and wherein said vitamins are selected from the group consisting of vitamin A, vitamin D, vitamin E, vitamin $B_{12}$, riboflavin, niacin, pantothenic acid, thiamine, choline, folic acid, biotin, vitamin K, vitamin C, and a combination thereof, and wherein said minerals are selected from the group consisting of cobalt, copper, iron, manganese, zinc, selenium, and a combination thereof.

8. The composition of claim 7, wherein said microorganisms are contained within said inner capsule and wherein said nutritional supplement is contained outside of said inner capsule.

9. The composition of claim 7, wherein said nutritional supplement is contained within said inner capsule and wherein said microorganisms are contained outside of said inner capsule.

10. The composition of claim 9, wherein said microorganisms are one or more of *Lactobacillus acidophilus, Lactobacillus lactis, Lactobacillus casei, Streptococcus faecium*, or *Pediococcus cerevisiae*.

11. The composition of claim 7, wherein said dissolvable shell of said outer capsule is gelatin and wherein said dissolvable shell of said inner capsule is gelatin.

12. The composition of claim 7, wherein said bacteria are the species *Bifidobacterium longum*.

13. The composition of claim 7, wherein said Bifidobacterium bacteria are present at a level of about $1.7 \times 10^9$ to about $4.5 \times 10^9$ CFU/capsule at the time of consumption.

14. The composition of claim 7, wherein said Propionibacterium are present at a level of about $2.5 \times 10^{11}$ to about $1.2 \times 10^{12}$ CFU/capsule at the time of consumption.

15. The composition of claim 14, wherein said Propionibacterium is *Propionibacterium freudenreichii*.

16. The composition of claim 7, wherein said fungus is the species *Aspergillus oryzae*.

17. The composition of claim 16, wherein said *Aspergillus oryzae* are present at a level of about $2 \times 10^7$ to about $4 \times 10^7$ CFU/capsule at the time of consumption.

18. The composition of claim 7, wherein said *Saccharomyces cerevisiae* is present at a level of about $13 \times 10^9$ to about $50 \times 10^9$ CFU/capsule.

19. The composition of claim 7, wherein said microorganisms are *Lactobacillus acidophilus, Lactobacillus lactis, Lactobacillus casei, Streptococcus faecium, Pediococcus cerevisiae* and *Saccharomyces cerevisiae*.

20. The composition of claim 7, wherein said microorganisms are *Lactobacillus acidophilus, Lactobacillus lactis, Lactobacillus casei, Streptococcus faecium, Pediococcus cerevisiae* and *Bifidobacterium longum*.

21. The composition of claim 7, wherein said microorganisms are *Propionibacterium freudenreichii*.

22. The composition of claim 21, wherein said nutritional supplement is vitamin A.

23. The composition of claim 21, wherein said nutritional supplement is vitamin A and wherein said vitamin A is admixed with humic acid.

24. The composition of claim 7, wherein said microorganisms are *Saccharomyces cerevisiae, Aspergillus oryzae* and *Propionibacterium freudenreichii*.

25. The composition of claim 7, wherein said microorganisms are *Saccharomyces cerevisiae, Aspergillus oryzae, Propionibacterium freudenreichii, Lactobacillus acidophilus, Lactobacillus lactis, Lactobacillus casei, Streptococcus faecium* and *Pediococcus cerevisiae*.

26. The composition of claim 7, wherein said microorganisms are *Lactobacillus acidophilus, Streptococcus faecium* and *Lactobacillus casei*.

27. The composition of claim 7, wherein said nutritional supplement is admixed with an acceptable feed grade carrier.

28. The composition of claim 27, wherein said feed grade carrier is kelp.

29. A method for providing a dietary supplement to a food-producing animal, comprising the steps of administering orally to said animal a double capsule having an inner gelatin capsule and an outer gelatin capsule enclosing said inner gelatin capsule, said double capsule including a nutritional supplement therein, said double capsule further including viable gastrointestinal microorganisms therein, said nutritional supplement partitioned from said microorganisms; wherein said microorganisms are rendered nonviable when said nutritional supplement and said microorganisms are stored in a bolus or single capsule formulation; said microorganisms including one or more of *Lactobacillus acidophilus, Lactobacillus lactis, Lactobacillus casei, Streptococcus faecium, Pediococcus cerevisiae, Bifidobacterium longum*, live cell yeast *Saccharomyces cerevisiae, Aspergillus oryzae* or *Propionibacterium freudenreichii*; said nutritional supplement selected from the group consisting of vitamins, minerals, and a combination of thereof, and wherein said vitamins are selected from the group consisting of vitamin A, vitamin D, vitamin E, vitamin $B_{12}$, riboflavin, niacin, pantothenic acid, thiamine, choline, folic acid, biotin, vitamin K, vitamin C, and a combination thereof, and wherein said minerals are selected from the group consisting of cobalt, copper, iron, manganese, zinc, selenium, and a combination thereof.

30. A dietary adjunct composition comprising:
    a) a double capsule, said double capsule including an inner capsule and an outer capsule spaced apart and enclosing said inner capsule, said inner capsule including a dissolvable gelatin shell, said outer capsule including a dissolvable gelatin shell, b) viable microorganisms within said double capsule, wherein said microorganisms include one or more of *Lactobacillus acidophilus, Lactobacillus lactis, Lactobacillus casei, Streptococcus faecium, Pediococcus cerevisiae, Bifidobacterium longum*, live cell yeast *Saccharomyces cerevisiae, Aspergillus oryzae* or *Propionibacterium freudenreichii*; and c) a nutritional supplement within said double capsule, said nutritional supplement separated from said microorganisms by said gelatin shell of said inner capsule, wherein said nutritional supplement is selected from the group consisting of vitamins, minerals, and a combination of thereof, and wherein said vitamins are selected from the group consisting of vitamin A, vitamin D, vitamin E, vitamin $B_{12}$, riboflavin, niacin, pantothenic acid, thiamine, choline, folic acid, biotin, vitamin K, vitamin C, and a combination thereof, and wherein said minerals are selected from the group consisting of cobalt, copper, iron, manganese, zinc, selenium, and a combination thereof.

31. The composition of claim 30, wherein said microorganisms are contained within said inner capsule and wherein said nutritional supplement is contained outside of said inner capsule.

32. The composition of claim 30, wherein said nutritional supplement is contained within said inner capsule and wherein said microorganisms are contained outside of said inner capsule.

* * * * *